United States Patent [19]

Holmes

[11] Patent Number: 5,403,717
[45] Date of Patent: Apr. 4, 1995

[54] DIAGNOSIS OF PREMALIGNANT OR MALIGNANT CONDITIONS OF HUMAN SECRETORY EPITHELIA

[75] Inventor: Eric H. Holmes, Bothell, Wash.

[73] Assignee: Pacific Northwest Research, Seattle, Wash.

[21] Appl. No.: 989,495

[22] Filed: Dec. 10, 1992

Related U.S. Application Data

[63] Continuation of Ser. No. 508,693, Apr. 9, 1990, abandoned, which is a continuation-in-part of Ser. No. 84,302, Aug. 11, 1987, Pat. No. 4,971,905.

[51] Int. Cl.$^6$ .................... C12Q 1/48; G01N 33/574
[52] U.S. Cl. ...................... 435/7.23; 435/15; 436/64; 436/71; 436/87; 436/813
[58] Field of Search ............ 435/7.23, 15; 436/64, 436/71, 87, 813

[56] References Cited

U.S. PATENT DOCUMENTS

| | | | |
|---|---|---|---|
| 4,389,392 | 6/1983 | Adachi | 436/501 |
| 4,471,057 | 9/1984 | Koprowski et al. | 436/518 |
| 4,752,569 | 6/1988 | Terasaki et al. | 435/7.23 |
| 4,757,003 | 7/1988 | Matsumoto et al. | 435/7.23 |
| 4,851,511 | 7/1989 | Hakamori et al. | 530/387 |
| 4,873,188 | 10/1989 | Hellstrom et al. | 435/7.23 |
| 4,971,905 | 11/1990 | Holmes | 435/15 |
| 4,994,374 | 2/1991 | Nishikawa et al. | 435/15 |

FOREIGN PATENT DOCUMENTS

| | | |
|---|---|---|
| 0272603 | 6/1988 | European Pat. Off. |
| 0387875 | 9/1990 | European Pat. Off. |
| 8902474 | 3/1989 | WIPO |
| 9005304 | 5/1990 | WIPO |

OTHER PUBLICATIONS

E. H. Holmes et al, *Jour. Biol. Chem.*, 262, 15649–15658, 1987.

S. Hakamori et al, *Jour. Nat. Cancer Inst.*, 71, 231–251, 1983.

F. W. Symington et al, *Molec. Immunol.*, 21, 877–882, 1984.

*Primary Examiner*—David Saunders
*Attorney, Agent, or Firm*—Stephen M. Evans; David L. Garrison

[57] ABSTRACT

A method for diagnostic or prognostic monitoring of premalignant or malignant conditions of human secretory epithelia, particularly colonic epithelia, by determining the extent of expression of a $\beta$1-3N-acetylglucosaminyltransferase is described. Associated with the expression of a wide variety of carbohydrate antigens in adenocarcinomas is the induction of $\beta$1-3N-acetylglucosaminyltransferase in epithelial cells. This enzyme is not found in normal, healthy adult colonic epithelial cells and thus indicates a novel and potentially sensitive method for screening the disease status of individuals.

15 Claims, 16 Drawing Sheets

1 2 3 4 5 6 7 8 9 10 11 12 13 14

1 2 3 4 5 6 7 8 9 10

1 2 3 4 5 6 7 8 9 10

1 2 3 4 5 6 7 8 9 10

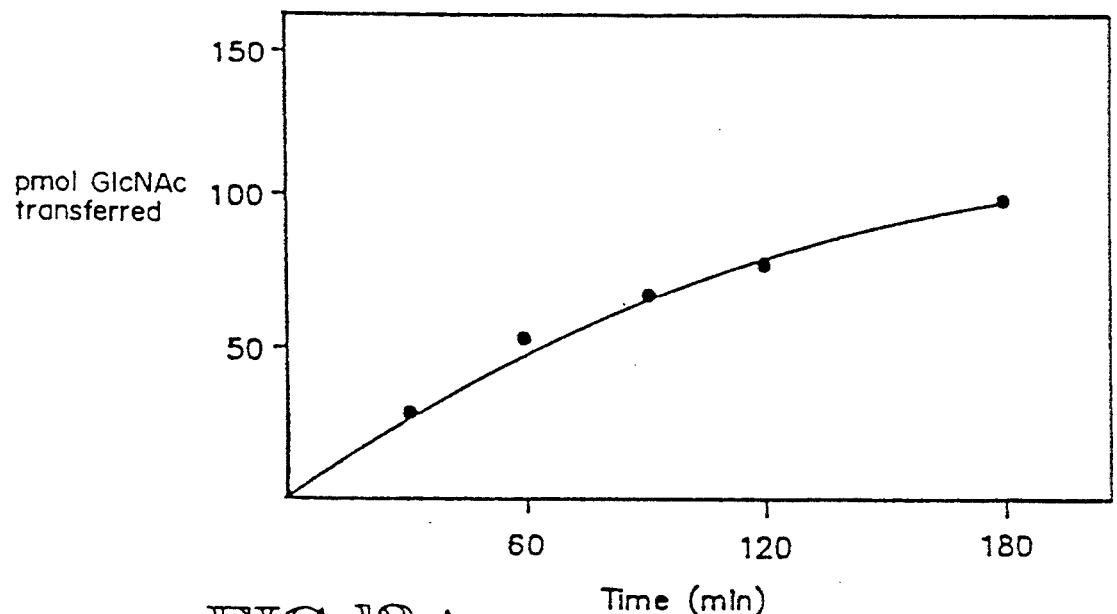
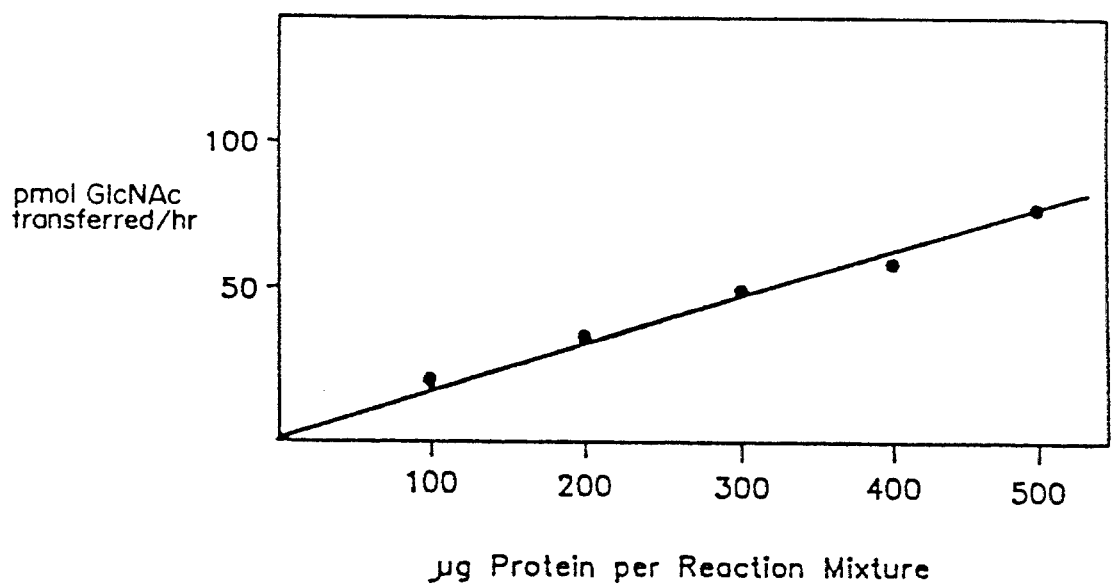
FIG. 13A
FIG. 13B

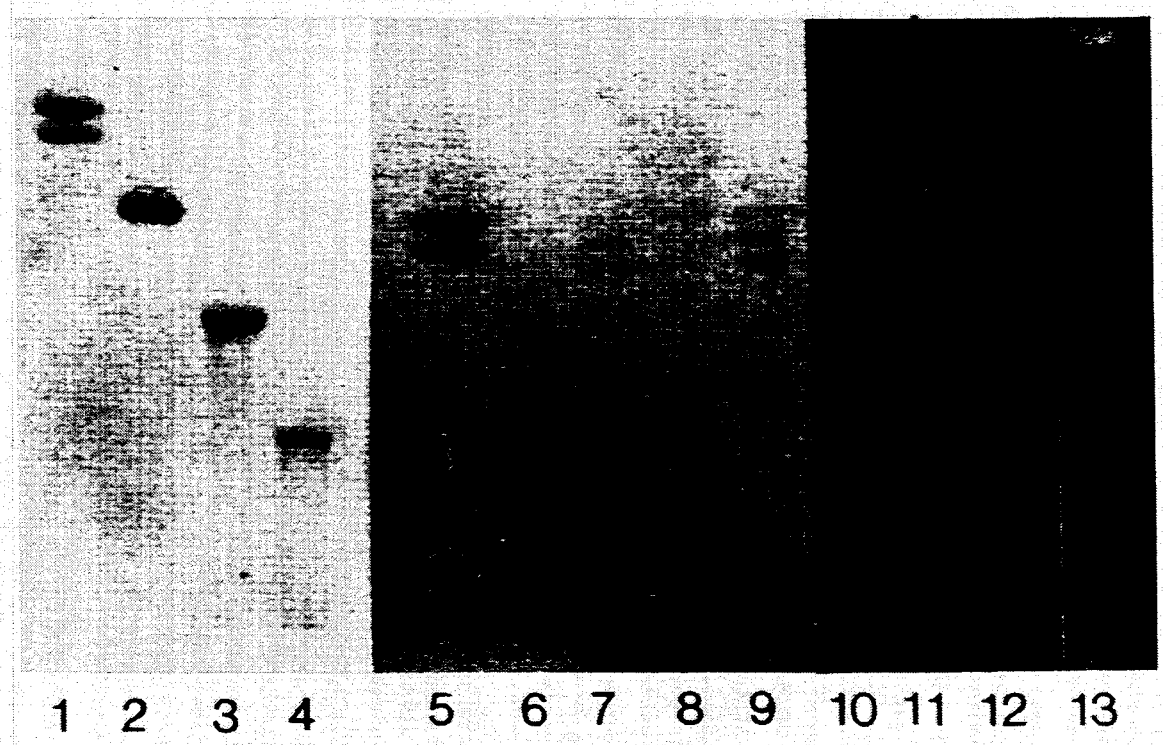

DIAGNOSIS OF PREMALIGNANT OR MALIGNANT CONDITIONS OF HUMAN SECRETORY EPITHELIA

This is a continuation of application Ser. No. 07/508,693, filed on Apr. 9, 1990, now abandoned, which was a continuation-in-part of then application Ser. No. 07/084,302, filed on Aug. 11, 1987, now issued as U.S. Pat. No. 4,971,905. The invention was made with Government support and the Government may have certain rights in the invention.

FIELD OF THE INVENTION

This invention relates to the detection of premalignant and malignant conditions of human tissues by analyzing and monitoring a specific enzymatic lesion responsible for characteristic changes in carbohydrate antigens expressed at the cell surface and released into serum.

BACKGROUND OF THE INVENTION

A variety of cases of both spontaneously occurring human cancers and experimental cancers in animals have been characterized as possessing tumor associated carbohydrate markers. Carbohydrate antigens carrying the $Le^x$ determinant (Gal$\beta$1-4[Fuc$\alpha$1-3]GlcNAc-) have been found to accumulate in large quantity in human adenocarcinomas. A collection of carbohydrate structures have been determined that have in common the presence of one or more $\alpha$1-3 linked fucose residues on GlcNAc, the hallmark of the $Le^x$ determinant structure. Further derivatives of the $Le^x$ structure have been demonstrated. The presence of $\alpha$1-3 linked fucose residues on both $\alpha$2-3 and $\alpha$2-6 terminally sialylated oligosaccharides have given rise to the sialyl-$Le^x$ determinant structure. In addition, $\alpha$1-3 fucosylation of blood group H structures have given rise to the $Le^y$ and trifucosyl $Le^y$ determinants.

With the advent of monoclonal antibody technology, a variety of highly specific antibodies have been generated which are directed to many of these related carbohydrate structures. Monoclonal antibodies specific for $Le^x$ and sialyl-$Le^x$ determinant carrying structures have been used for immunostaining tissue sections from normal human fetal and adult tissues as well as human adenocarcinomas. The antibody FH4 (specific for di- or trimeric $Le^x$ determinant) strongly stained a variety of human adenocarcinomas and fetal gastrointestinal and pulmobronchial epithelia during organogenesis. In adult tissues very little staining was observed. Only a small number of normal cells, such as parietal cells of gastric epithelia and Paneth's cells of intestinal mucosa, were positively stained.

Localization and distribution of the sialyl-$Le^x$ antigen has been studied using the sialyl-$Le^x$ determinant specific antibody FH6. These results indicated that a large variety of embryonic and fetal tissues showed positive staining particularly in the epithelial cell layer, however, no staining was observed in various normal adult tissues. Positive staining was also observed in a variety of cancer tissues tested. More recently, the expression of the $Le^y$ antigen has been studied in premalignant and malignant lesions of human colonic epithelium. These results indicated that $Le^y$ was expressed in colorectal adenocarcinomas and in colonic polyps which showed a greater degree of dysplasia. These results indicate that expression of a variety of glycolipids containing internal $\alpha$1-3 linked fucose residues on GlcNAc is associated with fetal development and oncogenesis in these tissues and such expression is oncofetal. Another related class of carbohydrate antigens that have been described as tumor-associated contain $\alpha$1-4 linked fucose residues on GlcNAc. These are isomeric structures of the $Le^x$ structures in that they differ in the linkage position of the galactose and fucose residues. These structures ($Le^a$) are part of the Lewis blood group system and are expressed in human cancers in association with the Lewis antigen status of the individual. The most highly studied antigen in this group is an $\alpha$2-3 sialylated form of the $Le^a$ antigen. An antibody, CA 19-9, specific for this structure has an apparent specificity for gastrointestinal and pancreatic cancer.

These related antigens expressing $\alpha$1-3 or $\alpha$1-4 fucose residues are derivatives of a commonly found core carbohydrate structure called the lactoseries. Structures containing $\beta$1-3 linked terminal Gal residues and $\alpha$1-4 linked fucose residues represent type 1 chain structures while terminal $\beta$1-4 Gal residues which can carry $\alpha$1-3 linked fucose residues are type 2 chain structures. Study of these antigens have indicated that the expression of both type 1 and type 2 chain based antigens are considered to be oncofetal in human colonic tissues since they are expressed at certain stages of normal development, decrease greatly in adult tissues, and re-appear in association with oncogenesis.

The great diversity of structures that occur in association with oncogenesis based on lacto-series chains along with the serologic diversity of individuals have so far prevented the finding of a single antibody which could recognize with great fidelity a premalignant or malignant condition necessary for diagnostic screening. This has limited the potential of the use of these carbohydrate structures in defining the disease status. The presence of a complex diversity of related structures in premalignant and malignant tissues tend to obscure the specific biochemical event that is responsible for their synthesis. Identification and exploitation of the specific lesion responsible for expression of both type 1 and 2 lacto-series chain structures could give rise to a general and sensitive process for survey of the disease status of any individual irrespective of their serological status. This would represent obvious improvements in the use of carbohydrate structures as sentinals for early stages in oncogenesis. The discoveries herein show results which indicate an alteration common to all colonic adenocarcinomas responsible for the formation of this complex series of carbohydrate antigens. This forms the basis of a method for diagnostic or prognostic screening of individuals which would represent a significant improvement over current technology.

SUMMARY OF THE INVENTION

This invention provides a method and process for identification of synthesis of carbohydrate antigens associated with many human tumors which would have important diagnostic applications. Formation of all type 1 and 2 lacto-series chain based antigens found to be tumor-associated in human adenocarcinomas result as a consequence of activation of a normally unexpressed $\beta$1→3N-acetylglucosaminyltransferase. This enzyme, in combination with a variety of normally expressed glycosyltransferases, gives rise to abundant quantities (in terms of both diverse structures and chemical amounts) of tumor associated antigens that are expressed at premalignant and malignant stages of oncogenesis. A sensitive survey of the disease status may be achieved by determining the extent of the expression of this activity through a variety of potential means. These include activity present in serum or biopsy tissues, the amount of $\beta 1\text{-}3$ linked GlcNAc residues in serum or tissue based carbohydrate structures, or other means to assess the expression of this activity. One method for diagnostic or prognostic detection of a cancerous disease state in secretory epithelia contemplated utilizes analysis of $\beta 1 \rightarrow 3$N-acetylglucosaminyltransferase expression in a test specimen by indirect detection or quantitation of the amount or presence of $\beta 1 \rightarrow 3$inked GlcNAc residues in glycoproteins or glycolipids using either broadly specific single antibodies reactive with two or more lacto-series carbohydrate structures to show the presence and quantity of said residues. Examples of suitable antibodies reactive with such carbohydrate epitopes include $LcOse_4$, $IV^3NeuAcLcOse_4$, $IV^3NeuAcIII^4FucLcOse_4$, $III^4FucLcOse_4$, $IV^2FucLcOse_4$, $III^4IV^2Fuc_2LcOse_4$, $IV^3\alpha GalIII^4IV^2Fuc_2\text{-}LcOse_4$, $IV^3\alpha GalNAcIII^4IV^2Fuc_2LcOse_4$, $nLcOse_4$, $IV^3NeuAcnLcOse_4$, $IV^6NeuAcnLcOse_4$, $IV^3NeuAcIII^3FucnLcOse_4$, $VI^3NeuAcIII^3V^3Fuc_2n\text{-}LcOse_6$, $III^3FucnLcOse_4$, $III^3V^3Fuc_2nLcOse_6$, $IV^2FucnLcOse_4$, $III^3IV^2Fu_2nLcOse_4$, $III^3V^3VI^2Fuc_3n\text{-}LcOse_6$, $IV^3\alpha GalIII^3IV^2Fuc_2nLcOse_4$, and $IV^3\alpha Gal\text{-}NAcIII^3IV^2Fuc_2nLcOse_4$.

BRIEF DESCRIPTION OF THE DRAWINGS

FIG. 1 shows thin layer chromatography profiles of neutral glycolipids from normal tissues and tumors and demonstrates the absence in normal adult colonic mucosa of significant quantities of $Le^x$ structures (FIG. 1B) or underivatized type 2 chain precursor structures (FIG. 1C). These structures are found in abundant quantity in neutral glycolipids from colonic adenocarcinoma tumors.

FIG. 6 is an immunofluorescence analysis which shows that the co-existence in normal mucosa of $\beta$1-4galactosyltransferase and $\alpha$1-3fucosyltransferase without the synthesis of Le$^x$ active structures is due to the expression of type 2 chain precursors in different cell populations of normal mucosa rather than those cells expressing fucosyltransferase activity. Analysis of tissue sections from normal human adult and fetal proximal colon are shown. FIGS. 6A and 6B, tissue immunofluorescence with Le$^x$ specific antibody FH3 after treatment of the sections with neuraminidase. FIGS. 6C and 6D, tissue immunofluorescence with anti-Le$^a$ antibody after neuraminidase treatment of the sections. FIGS. 6E and 6F tissue immunofluorescence with type 2 chain specific antibody 1B2 before neuraminidase treatment of the sections. FIGS. 6G and 6H, tissue immunofluorescence with antibody 1B2 after neuraminidase treatment of the sections. The sections were prepared as described under "Experimental Prodecures". Magnification 200 x.

FIG. 10 shows that expression of lacto-series antigens in normal colon mucosal tissue sections can be generated by supplying the tissue with precursor acceptors and sugar nucleotide donors. In situ biosynthesis of nLc4 from Lc3 is shown in tissue sections of normal adult colonic mucosa. The results shown are immunofluorescence of normal mucosal tissue sections after incubation with the N-acetyllactosaminyl residue specific antibody 1B2 followed by FITC-labelled rabbit anti-mouse secondary antibody.

FIG. 13 plots enzyme activity and shows that conditions for assay of β1→3N-acetylglucosaminyltransferase activity have been defined which yield results that are linear with respect to both time and protein concentration. FIG. 13A: Time course of transfer reaction. The standard reaction mixture was scaled up 6-fold in the presence of 2.4 mg protein. Aliquots, 0.05 ml each were withdrawn at the times indicated and the incorporation of labelled GlcNAc into lactosylceramide was quantitated. FIG. 13B: Effect of increasing protein concentration. The conditions were the same as described under "Experimental Procedures" except that the solubilized protein was varied from 100 to 500 μg per reaction mixture.

FIG. 14 is a high performance thin layer chromatographic analysis which shows that the β1→3N-acetylglucosaminyltransferase will transfer GlcNAc to structures containing a terminal galactose residue only if it is not derivatized by addition of other sugars such as fucose. Lane 1, standard lactosylceramide; lane 2, standard Lc$_3$; lane 3, standard nLc$_4$; lane 4, standard nLc$_6$; lane 5, autoradiograph of product from transfer of [$^{14}$C]-GlcNAc to lactosylceramide; lane 6, autoradiograph of product from transfer to nLc$_4$; lane 7, autoradiograph of product from transfer to Lc$_4$; lane 8, autoradiograph of product from transfer to nLc$_6$; lane 9, autoradiograph of products from transfer to endogenous acceptors; lane 10, immunostain analysis with antibody J1 with standard Lc$_3$; lane 11, immunostain analysis of acceptor lactosylceramide; lane 12, immunostain analysis of product from transfer of unlabelled GlcNAc to lactosylceramide; lane 13, immunostain analysis of products from transfer to endogenous acceptors. Standard glycolipids were visualized by orcinol spray. The solvent system was composed of CHCl$_3$:CH$_3$OH:H$_2$O, 60:35:8.

DESCRIPTION OF THE PREFERRED EMBODIMENT

Figure 1A:
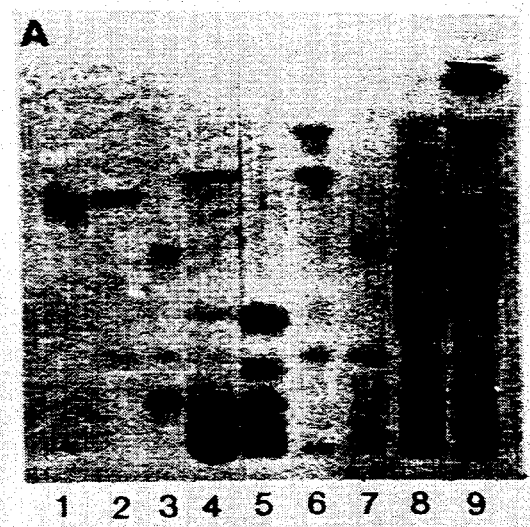
In FIG. 1A, neutral glycolipids of the indicated fractions are shown visualized by orcinol spray. Lane 1, standard $Lc_4$; lane 2, standard $nLc_4$; lane 3, standard $III^3V^3Fuc_2nLc_6$ and $III^3FucnLc_4$ (in terms of increasing mobility); lane 4, type "O" whole blood cell Folch upper neutral fraction; lane 5, normal human liver upper neutral fraction; lane 6, normal human colonic mucosa total neutral glycolipids; lane 7, NCI-H69 cell neutral glycolipids; lane 8, human colonic adenocarcinoma FT-620 neutral glycolipids; lane 9, human colonic adenocarcinoma TG-115 neutral glycolipids.
Figure 1B:
FIG. 1B, shows immunostain analysis of glycolipid fractions with the $Le^x$ specific antibody WHGS-29-1. Lane 1, standard $III^3V^3Fuc_2nLc_6$, $V^3FucnLc_6$, and $III^3FucnLc_4$ (in terms of increasing mobility); lane 2, type "O" whole blood cell upper neutral glycolipids; lane 3, normal human liver upper neutral glycolipids; lane 4, normal human colonic mucosa neutral glycolipids; lane 5, NCI-H69 cell neutral glycolipids; lane 6, neutral glycolipids from human colonic adenocarcinoma FT-620; lane 7, neutral glycolipids from human colonic adenocarcinoma TG-115.
Figure 1C:
FIG. 1C, shows immunostain analysis of glycolipid fractions with antibody 1B2 specific for type 2 chain core structures. Lane 1, standard $nLc_4$; lane 2, type "O" whole blood cell upper neutral glycolipids; lane 3, normal human liver upper neutral glycolipids; lane 4, neutral glycolipids from normal human colonic mucosa; lane 5, neutral glycolipids from NCI-H69 cells; lane 6, neutral glycolipids from human colonic adenocarcinoma FT-620; lane 7, neutral glycolipids from human colonic adenocarcinoma TG-115.
Figure 1D:
FIG. 1D shows immunostain analysis of glycolipid fractions with anti-$Le^a$ antibody. Lane 1, neutral glycolipids from human meconium; lane 2, type "O" whole blood cell upper neutral glycolipids; lane 3, normal human liver upper neutral glycolipids; lane 4, neutral glycolipids from normal human colonic mucosa; lane 5, neutral glycolipids from NCI-H69 cells; lane 6, neutral glycolipids from human colonic adenocarcinoma FT-620; lane 7, neutral glycolipids from human colonic adenocarcinoma TG-115. The plates were developed in a solvent system composed of $CHCl_3:CH_3OH:H_2O$, 56:38:10. Conditions of immunostain analysis were as described under "Experimental Procedures" below.

Pursuant to this invention the cellular expression of diagnostic type 1 and 2 lacto-series tumor-associated carbohydrate structures is detected by means to measure B1→3N-acetylglucosaminyltransferase action or activity. No single in vivo derived type 1 or type 2 lacto-series structure has complete specificity for premalignant or malignant status in human adenocarcinomas, although a wide variety of related structures are formed. The status of β1→3N-acetylglucosaminyltransferase activity or action which is activated in order to express all of these antigens in adenocarcinomas and is therefore the single enzymatic lesion responsible for the expression of type 1 and 2 chain based antigens is the most specific and universal sentinal for disease progression. Diagnostic and prognostic applications are shown which would yield a significant improvement over current technology.

As described in the following series of Examples, the carbohydrate structures found on both normal human colonic mucosa and derived colonic adenocarcinoma tumors and cell lines were characterized by extracting the cellular glycolipids with isopropanol:hexane:water (55:25:20), separation into neutral glycolipid and ganglioside fractions by chromatography on a DEAE-Sephadex column, and analysis by thin layer chromatography and thin layer chromatography immunostain procedures. These procedures showed that tumor cells and tissues contained a wide variety of lacto-series antigens which displayed diverse discrete antigenic determinants. These carbohydrate structures were almost undetectable in extracts from normal mucosal epithelial cells.

Further characterization of the differential biosynthesis of lacto-series carbohydrate structures in normal colonic mucosa and colonic adenocarcinoma cells and tumors by analysis of the biosynthetic enzymes involved in the synthesis of these carbohydrate structures yielded a novel finding. Despite the absence of fucosylated derivatives of lacto-series glycolipids in normal mucosal epithelia, a very high activity of a fucosyltransferase was found. However, normal adult colonic epithelial cells were shown by immunofluorescence staining on frozen tissue sections to lack type 2 lacto-series chain expression. Thus the absence of fucosylated derivatives of type 2 chains is due to the control of type 2 chain expression. The expression of these carbohydrate antigens has been considered to be oncofetal in nature in that they are expressed during normal development, are lost in adult tissues, and re-appear during oncogenesis in human colon. As a control, immunofluorescence staining of fetal colon indicated the abundant presence of type 2 chain precursors and the resultant fucosylated derivatives. This identified the key to the expression of the entire diverse class of tumor-associated antigens as control of expression of lacto-series core carbohydrate chains. Further characterization of the biosynthesis of lacto-series core chains by direct enzymatic analysis and analysis of in situ biosynthesis of lacto-series core chains in normal colonic epithelial cells by an immunohistological technique indicated that the key enzyme that is missing, or only very minimally expressed, in normal adult colonic epithelial cells is a β1→3-N-acetylglucosaminyltransferase responsible for the first committed step in lacto-series core chain synthesis.

As a consequence of this finding, it is clear that a more universal and potentially more sensitive diagnostic marker for premalignant and malignant conditions is the status of this β1→3-N-acetylglucosaminyltransferase in adult colonic tissues. Thus, screening of individuals for the status of this activity, the expression of this enzyme protein, or the direct or indirect analysis of the action of this enzyme by incorporation of β1→3 linked GlcNAc residues into lacto-series carbohydrate chains represents a new and useful basis for disease diagnosis. These diagnostic tests are comprised as follows. 1) Direct enzyme assay using a tissue or serum specimen as the enzyme source and transfer of a labeled donor sugar to an acceptor carbohydrate structure. 2) Determination of the level of enzyme expression of a sample in an immunoassay using antibodies against the enzyme. 3) Determination of the level of enzyme expression of a sample by labeled cDNA hybridization to mRNA derived from a tissue specimen and 4) Determination of the level of enzyme expression of a sample by immunoassay using broadly specific or mixtures of antibodies reactive with enzyme reaction products and/or further in vivo derivatives or using terminal β1→3-GlcNAc specific antibodies after first treating a specimen with hydrolytic enzymes to expose the β1→3-GlcNAc residue. With this information as a basis, this invention contemplates potential diagnostic applications of this marker. The following Examples are presented to illustrate the advantages of the present invention and to assist one of ordinary skill in making and using the same. The following Examples are not intended in any way to otherwise limit the scope of the disclosure or the protection granted by Letters Patent hereon.

FIRST SERIES OF EXAMPLES

The expression of a wide diversity of lacto-series antigens has been described to be associated with colonic adenocarcinomas. The nature of the control of the synthesis of these antigens in normal compared to premalignant or malignant tissues is essential to the understanding of this phenomenon and a key for use of these markers for diagnostic purposes.

To determine the nature of the expression of lacto-series carbohydrate antigens during oncogenesis in human tissues, normal human colonic mucosa was studied to determine its enzymatic content Of glycosyltransferases associated with lacto-series chain synthesis and its level of expression of lacto-series carbohydrate chains. Reported here is data which indicates that normal human adult mucosa contains the glycosyltransferase activities necessary to synthesize the tumor-associated $Le^x$ series of antigens, however, they are not formed. Data shows that the colonic mucosal epithelial cells (the precursor cells to colonic adenocarcinomas) in adult tissues are unable to synthesize type 2 lacto-series core chains thus preventing the expression of type 2 chain based tumor-associated antigens such as $Le^x$. Alteration of expression of type 2 core chains is thus the essential feature in expression of all type 2 chain based tumor-associated antigens in colonic adenocarcinomas.

EXAMPLE 1

Glycolipid Pattern in Normal Human Colonic Mucose and Colonic Adenocarcinomas

The glycolipid composition from cells of normal adult colonic mucosa was analyzed and compared with that from colonic adenocarcinoma tumors to demonstrate the qualitative differences between them along with the complexity of tumor-associated antigens present in tumor tissue.

Analysis of the glycolipid composition was performed by immunostain procedures utilizing specific antibodies with glycolipid fractions isolated from pooled mucosal tissue. Scraped mucosal tissue is comprised of epithelial cells as well as connective tissue and various inflamatory cells. The glycolipid profiles of normal colonic mucosa were compared with those of the human small cell lung carcinoma cell line NCI-H69 cells and human colonic adenocarcinoma tumors and shown in FIG. 1. The greatest chemical quantity of neutral glycolipids isolated from normal mucosal tissue migrates in the area of CDH and $Gb_3$. Minor bands are also observed that migrate with tetraglycosylceramide and longer chain derivatives (FIG. 1A, lane 6). In contrast, most of the glycolipid bands isolated from NCI-H69 cells and human adenocarcinoma tumors FT-620 and TG-115 are slower migrating components (lanes 7–9). FIG. 1$b$ shows results of immunostain analysis with the $Le^x$ determinant specific antibody WGHS-29-1. A similar pattern of bands is observed for glycolipids extracted from NCI-H69 cells and human colonic adenocarcinoma tumors FT-620 and TG-115 known to accumulate large quantities of $Le^x$ determinant carrying structures (lanes 5–7). In these glycolipid fractions, intense bands corresponding to $III^3FucnLc_4$, $V^3FucnLc_6$, $III^3V^3Fuc_2nLc_6$, and slower migrating bands are observed in each fraction. Many of these bands are normally found in small quantities in extracts from type "O" whole blood from leukocytes or normal human liver as shown in lanes 2 and 3, respectively. Only very weak reactive glycolipid bands are found in extracts of normal colonic mucosa that co-migrate with $III^3V^3Fuc_2nLc_6$ and a slower migrating band. No staining of faster migrating bands is observed. Immunostain analysis with the $Le^y$ specific antibody AH6 indicated no staining of glycolipids from normal mucosal fractions (results not shown). These results indicate that almost no $\alpha$1-3 fucose containing structures are present in the neutral glycolipid fraction of normal colonic mucosa. Immunostain analysis with antibody 1B2, specific for type 2 chain structures $nLc_4$, $nLc_6$, $nLc_8$, etc., is shown in FIG. 1$c$. Bands corresponding to $nLc_4$, $nLc_6$, and longer chain structures are found in the neutral glycolipid fractions of NCI-H69 cells, FT-620, and TG-115 (lanes 5–7). But with normal colonic mucosa, only a weak band corresponding to $nLc_6$ is found (lane 4).

Type 1 chain fucosylated derivatives were readily detected with anti-$Le^a$ antibody (FIG. 1$d$). Strong staining corresponding to $III^4FucLc_4$ is found in the glycolipid fraction from type "O" RBC's (lane 2), FT-620 (lane 6), and TG-115 (lane 7). In addition, strong staining is also found corresponding to $III^4FucLc_4$ and a slower migrating band in the glycolipid fraction of normal colonic mucosa (lane 4) indicating the presence of type 1 chain containing structures.

Figure 2:
FIG. 2 shows that gangliosides isolated from normal adult colonic mucosa contain most of the type 2 chain core structures present in normal mucosa. Immunostain analysis of desialylated gangliosides of normal human colonic mucosa and NCI-H69 cells are shown with the type 2 chain specific antibody 1B2. Lane 1, standard $nLc_4$; lane 2, desialylated gangliosides from type "O" whole blood cells; lane 3, desialylated gangliosides from NCI-H69 cells; lane 4, desialylated gangliosides from normal human colonic mucosa. The plate was developed in a solvent composed of $CHCl_3:CH_3OH:H_2O$, 56:38:10.

These results indicate that only a small quantity of type 2 chain structures, either fucosylated or nonfucosylated, are found in the neutral glycolipid fraction from normal colonic mucosa. Identification of type 2 chain structures present in the ganglioside fraction from normal mucosa was performed with antibody 1B2 after desialylation with 1% acetic acid at 100° C. for 1 hour. These results are shown in FIG. 2. Staining of multiple bands corresponding to $nLc_4$, $nLc_6$, and slower migrating glycolipids is observed after hydrolysis of standard type "O" RBC gangliosides (lane 2), and of a band corresponding to $nLc_4$ and weak slower migrating bands with hydrolyzed gangliosides from NCI-H69 cells (lane 3). In addition, bands corresponding to $nLc_4$ and $nLc_6$ and a weaker slower band are found with hydrolyzed gangliosides from normal colonic mucosa (lane 4). Previous results (J. Biol. Chem., 261, 3737–3743 (1986)) have indicated that gangliosides based on type 2 chains can be fucosylated to yield sialyl-$Le^x$ derivatives. Immunostain analysis of the desialylated gangliosides from normal colonic mucosa using the $Le^x$ determinant specific antibody WGHS-29-1 was negative indicating the absence of sialyl $Le^x$ structures in this fraction (results not shown). These results indicate that type 2 lacto-series chains are present in normal colonic mucosa in very low quantity and that almost all of these type 2 chain based glycolipids in the normal colonic mucosa are present as either $\alpha$2-3 or $\alpha$2-6 sialyl derivatives.

EXAMPLE 2

$\alpha$1-3Fucosyltransferase Activity of NCI-H69 Cells and Normal Human Colonic Mucosa One of the most commonly observed tumor-associated carbohydrate antigens found in adenocarcinomas is the $Le^x$ antigen. This is actually a series of structures containing $\alpha$1-3 linked fucose residues on GlcNAc residues of type 2 lacto-series core chains. The α1-3 linked fucose on GlcNAc is also found on other more complex type 2 chain derivatives such as Le$^y$ structures and sialyl-Le$^x$ structures. Essentially all of these α1-3 fucosyl derivatives have been described as being tumor markers or markers of premalignant tissues. The common feature of α1-3 fucosyl residues has drawn attention to the α1-3fucosyltransferase whose activation might be the enzymatic lesion responsible for induction of these α1-3 fucosyl structures in adenocarcinomas. To investigate this further, the α1-3fucosyltransferase activity was studied, in normal mucosa and compared to that from NCI-H69 cells which accumulate large quantities of α1-3 linked fucose structures.

TABLE 1

α1-3 Fucosyltransferase activity of crude homogenates of NCI-H69 cells and normal human colonic mucosa.

| Extract Source | pmol/hr/mg protein |
| --- | --- |
| NCI-H69 cells | 720. |
| Normal colonic mucosa case #1 | 167. |
| Normal colonic mucosa case #2 | 299. |
| Normal colonic mucosa case #3 | 199. |

Assays were performed as described under "Experimental Procedures" using nLc$_4$ as the acceptor glycolipid.

Figure 3:
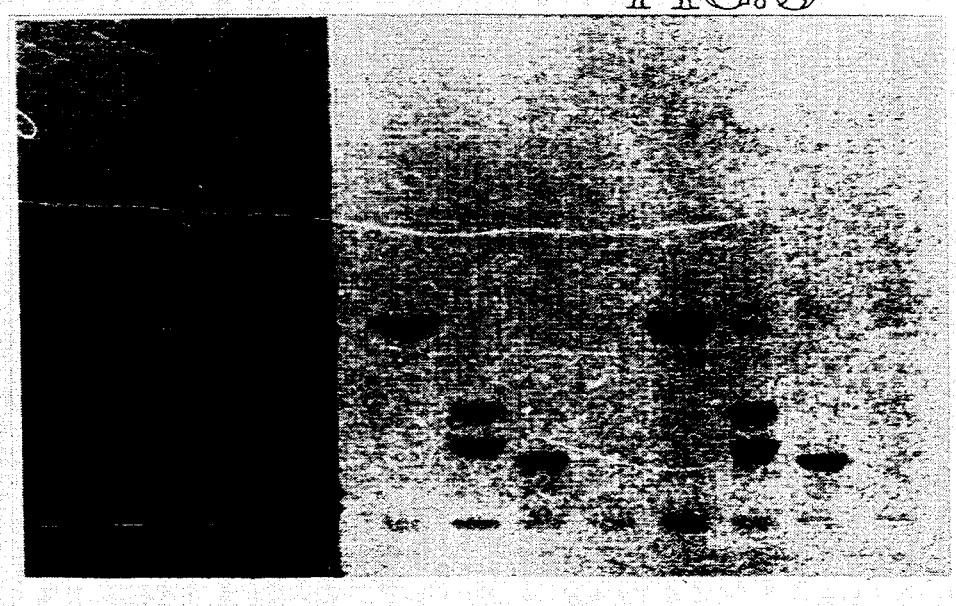
FIG. 3 is a thin layer chromatography analysis showing that fucosyltransferase from normal mucosa, similar to that from human small cell lung carcinoma cells, transfers fucose in $\alpha 1\text{-}3$ linkage to type 2 chain structures to form mono- or poly-fucosyl derivatives. Products are formed from a variety of acceptor glycolipids with type 2 chain by fucosyltransferase from normal human colonic mucosa and NCI-H69 cells. Lane 1, standard $nLc_4$; lane 2, standard $III^3FucnLc_4$; lane 3, standard $V^3FucnLc_6$; lane 4, standard $III^3V^3Fuc_2nLc_6$. Lanes 5–8 are TLC profiles of products from transfer of $[^{14}C]$- fucose to the indicated glycolipid catalyzed by fucosyltransferase from normal human colonic mucosa. Lane 5, product from transfer to $nLc_4$; lane 6, product from transfer to $nLc_6$; lane 7, product from transfer to $V^3FucnLc_6$; lane 8, product from transfer to glycolipids endogenous to the enzyme fraction. Lanes 9–12 are TLC profiles of products from transfer of $[^{14}C]$fucose to the indicated glycolipid catalyzed by the solubilized enzyme from NCI-H69 cells. Lane 9, product from transfer to $nLc_4$; lane 10, product from transfer to $nLc_6$; lane 11, product from transfer to $V^3FucnLc_6$; lane 12, product from transfer to glycolipids endogenous to the solubilized enzyme. The products were synthesized as described under "Experimental Procedures" using 30 μg of acceptor glycolipid. The plate was developed in a solvent system composed of $CHCl_3:CH_3OH:H_2O$, 56:38:10. Standard glycolipids were visualized by orcinol spray. The location of the $^{14}C$-labelled bands was determined by autoradiography.
Figure 4:
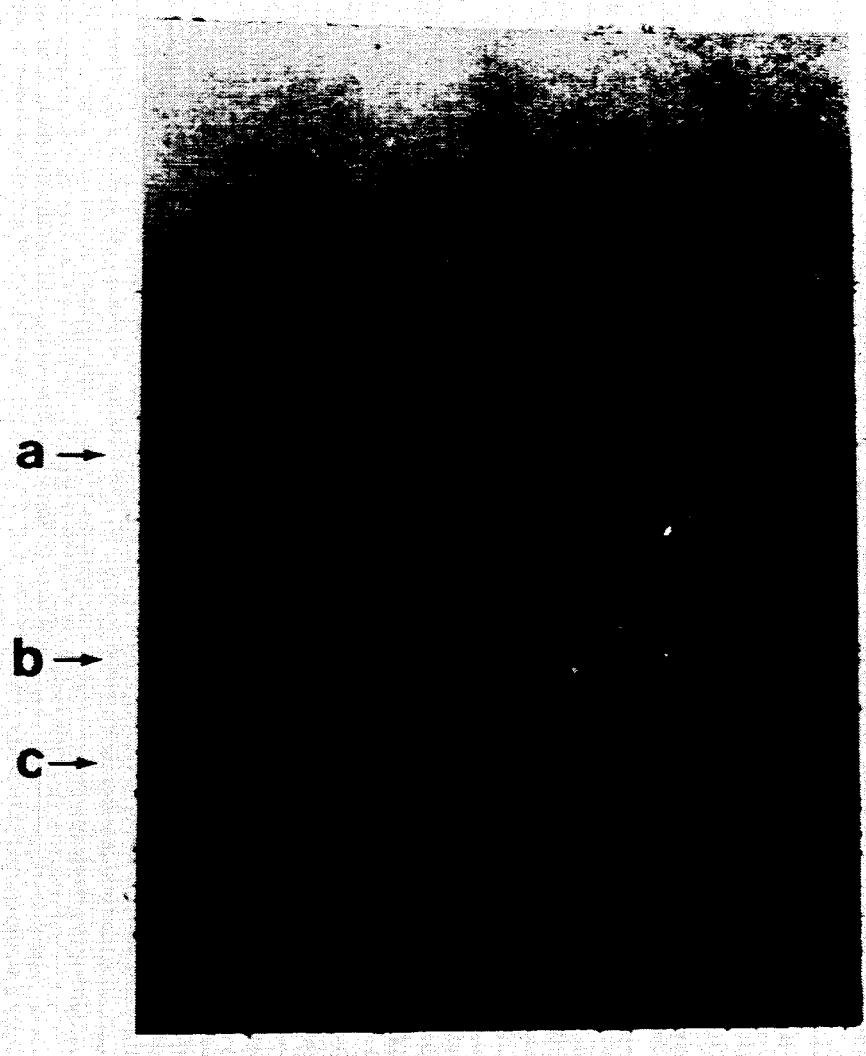
FIG. 4 is an immunostain analysis showing that the fucosyltransferase from normal mucosa is indeed transferring fucose in $\alpha 1\text{-}3$ linkage by virtue of the formation of $Le^x$ active structures. Reaction products are formed from transfer of fucose from GDPfucose catalyzed by fucosyltransferase from normal human colonic mucosa and NCI-H69 cells with the monoclonal antibody WHGS-29-1. Lane 1, standard $III^3FucnLc_4$ (a), $V^3FucnLc_6$ (b), $III^3V^3Fuc_2nLc_6$ (c); lanes 2–4 are products from transfer by enzyme from NCI-H69 cells; lane 2, product from transfer to $nLc_4$; lane 3, immunostain profile of glycolipids endogenous to the enzyme fraction; lane 4 products from transfer to $nLc_6$. Lanes 5–7 are products from transfer by enzyme from normal human colonic mucosa. Lane 5, product from nLc4; lane 6, immunostain of glycolipids endogenous to the mucosal fraction; lane 7, product from transfer to nLc6. The plate was developed in a solvent system composed of $CHCl_3:CH_3OH:H_2O$, 56:38:10. The conditions of immunostain analysis are as described under "Experimental Procedures".

Table 1 shows a comparison of the α1-3fucosyltransferase specific activity of crude homogenates from normal human colonic mucosa and the human small cell lung carcinoma cell line NCI-H69 with nLc$_4$ as the acceptor. Although the fucosyltransferase activity is highest in NCI-H69 cells, there is significant activity present in the scraped mucosal fraction where the specific activity of the different cases is decreased only 2- to 4-fold. FIG. 3 shows results of incorporation of $^{14}$C-fucose into acceptor nLc$_4$, nLc$_6$, and V$^3$FucnLc$_6$ catalyzed by normal mucosal and NCI-H69 cell homogenates. These results show that the TLC mobility of reaction products after transfer of $^{14}$C-fucose to nLc$_4$, nLc$_6$, or V$^3$FucnLc$_6$ by homogenates of NCI-H69 cells (lanes 9–12) is identical to results obtained when homogenates of normal mucosa were used as the enzyme source (lanes 5–8). Results of immunostain analysis of parallel reaction products after transfer of unlabelled fucose to acceptor nLc$_4$ and nLc$_6$ using the Le$^x$ determinant specific antibody WGHS-29-1 is shown in FIG. 4. The same pattern of staining is observed for normal mucosal reaction products (lanes 5–7) and NCI-H69 cell products (lanes 2–4) with the indicated acceptor glycolipids. In addition, these bands correspond to the products formed from transfer of $^{14}$C-fucose indicating that all of the products detected are α1-3 linked. Immunostain analysis of the reaction products with the H-specific antibody BE2 indicated no evidence for formation of α1-2 linked fucose structures (results not shown).

These results show that significant α1-3fucosyltransferase activity is found in normal colonic mucosa despite the lack of α1-3 fucose containing carbohydrate structures in the glycolipids extracted from normal mucosa as demonstrated in Example 1 above. The α1-3fucosyltransferase from normal mucosa was investigated further as shown below. Nature of the fucosyltransferase from normal adult colonic epithelia.

Both α1-3 (J. Biol. Chem., 260, 7619–7627 (1985); Eur. J. Biochem., 30., 269–277 (1972), Eur. J. Biochem., 130, 347–351 (1983)) and α1-¾ (J.Biol.,Chem., 256, 10456–10463 (1981), Biochem. Biophys. Res. Commun., 100, 1611–1618 (1981), FEBS Lett., 142, 77–80 (1982)) specific fucosyltransferases have been identified in human cells. The nature of this activity in normal colonic epithelia was determined by kinetic analysis of the reaction with different acceptor substrates. Table 2 shows the incorporation of $^{14}$C-fucose into either Lc$_4$, nLc$_4$, or mixed Lc$_4$ and nLc$_4$ catalyzed by enzyme fractions from NCI-H69 cells which contain a highly specific α1-3fucosyltransferase and normal colonic mucosa. The results indicate that a single α1-3 specific fucosyltransferase is found in NCI-H69 cells consistent with previous results (J.Biol. Chem., 260, 7619–7627 (1985)). Enzyme activities catalyzing transfer to both Lc$_4$ and nLc$_4$ are found in normal mucosal fractions. The activity with nLC$_4$ as acceptor yielded about 2-fold higher activity than when Lc$_4$ was the acceptor. This is essentially the same result previously found for the Le-gene specified fucosyltransferase from human milk (J. Biol. Chem., 256, 10456–10463 (1981)). Analysis of the activity when both Lc$_4$ and nLc$_4$ are mixed indicates that essentially all of the fucosyltransferase activity can be accounted for by a single enzyme, most probably the Le-gene specified fucosyltransferase, capable of transferring fucose in either α1-3 or α1-4 linkages.

TABLE 2

Substrate competition studies with fucosyltransferases from homogenates of NCI-H69 cells and normal human colonic mucosa

| | pmol [$^{14}$C]fucose transferred/hr/mg protein to: | | | | |
| --- | --- | --- | --- | --- | --- |
| | | | | calculated values for: | |
| Enzyme Source | Lc$_4$ | nLc$_4$ | Lc$_4$ + nLc$_4$ | One enzyme | Two enzymes |
| NCI-H69 cells | ND | 1208. | 1195. | | |
| Normal colonic mucosa case #1 | 83. | 297. | 177. | 179. | 380. |
| Normal colonic mucosa case #2 | 270. | 551. | 418. | 386. | 821. |
| Normal colonic mucosa case #3 | 95. | 210. | 158. | 144. | 305. |

Reaction mixtures were as described under "Experimental Procedures" and contained 40 μg of Lc$_4$, nLc$_4$, or 40 μg of both Lc$_4$ and nLc$_4$. Calculated values for activity with mixed acceptor composition were determined using the following equations:

Two enzymes $v_t = v_a + v_b$

One enzyme $v_t = \dfrac{V_a a/K_a + V_b b/K_b}{1 + a/K_a + b/K_b}$

ND = none detected

This indicates that expression of α1-3 fucose containing structures in both normal colonic mucosa and in derived adenocarcinomas is regulated by the Le gene and thus depends on the Lewis blood group status of the individual. This has already been shown for type 1 chain based Le$^a$ antigens which also accumulate in adenocarcinomas (see Example 6 for discussion of type 1 chain based antigens). Additionally, this data indicates that expression of fucosyltransferase activity is independent of synthesis of α1-3 linked fucose containing tumor-associated carbohydrate antigens.

EXAMPLE 3

UDPgalactose:Lc$_3$ Galactosyltransferase Activity of Normal Colonic Mucosa and NCI-H69 Cells To understand the basis for the expression of type 2 chain lacto-series antigens in adenocarcinomas, information relating to the biosynthetic capacity of normal mucosa and adenocarcinoma tumors for type 2 core structures is necessary. This was investigated by determining the enzyme activity associated with type 2 chain synthesis from .its immediate precursor Lc$_3$ which is also the precursor of type 1 chain based antigens which have been found on normal mucosal epithelial cells. This enzyme is a β1-4galactosyltransferase and was studied as shown below.

TABLE 3

UDPGalactose:Lc$_3$ Galactosyltransferase activity of NCI-H69 cells and normal human colonic mucosa.

| Enzyme Source | pmol galactose transferred/hr/mg protein | |
|---|---|---|
| | as Lc$_4$ | as nLc$_4$ |
| NCI-H69 cells | ND | 567. |
| Normal colonic mucosa case #1 | 300. | 459. |
| Normal colonic mucosa case #2 | 432. | 772. |
| Normal colonic mucosa case #3 | 280. | 445. |

Figure 5:
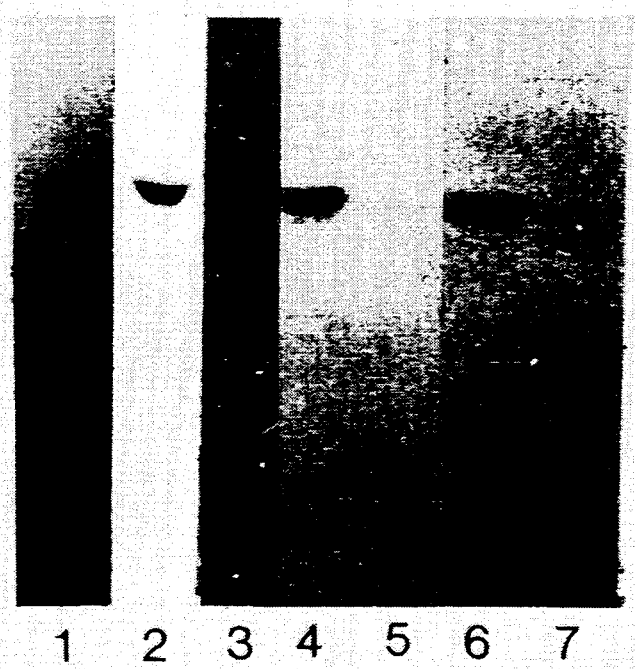
FIG. 5 is a thin layer chromatography and immunostain analysis which shows that a $\beta$1-4galactosyltransferase is found in normal mucosa and that this enzyme can synthesize type 2 chain precursor structures. Products are shown from transfer of galactose to Lc3 catalyzed by enzyme fractions from NCI-H69 cells and normal human colonic mucosa. Lane 1, standard nLc4; lane 2, autoradiograph of product formed from transfer of $^{14}$C-Gal to Lc3 catalyzed by enzyme from NCI-H69 cells; lane 3, autoradiograph of products formed catalyzed by normal human colonic mucosa; lane 4, immunostain analysis of reaction products from transfer of galactose to Lc3 by enzyme from NCI-H69 cells with antibody 1B2. Lane 5, immunostain profile of products of transfer to glycolipids endogenous to the enzyme from NCI-H69 cells; lane 6, immunostain profile of products from transfer to Lc3 catalyzed by human colonic mucosa; lane 7, immunostain profile of products from transfer to glycolipids endogenous to human colonic mucosa. The plates were developed in a solvent system composed of $CHCl_3:CH_3OH:H_2O$, NO H.R.(60:35:8). Standard nLc4 was visualized by orcinol spray. The conditions of immunostain analysis were as described under "Experimental Procedures".
Figure 6A:
FIG. 6A, 6C, 6E, and 6G are results from adult tissues.
Figure 6B:
FIGS. 6B, 6D, 6F and 6H are results from fetal tissues at 120 days gestation.
Figure 6C:
Figure 6D:
Figure 6E:
Figure 6F:
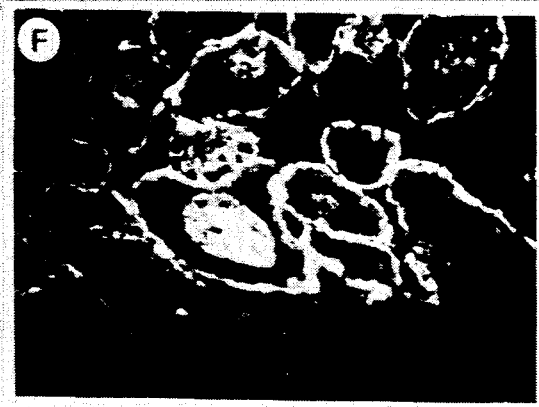
Figure 6G:
Figure 6H:
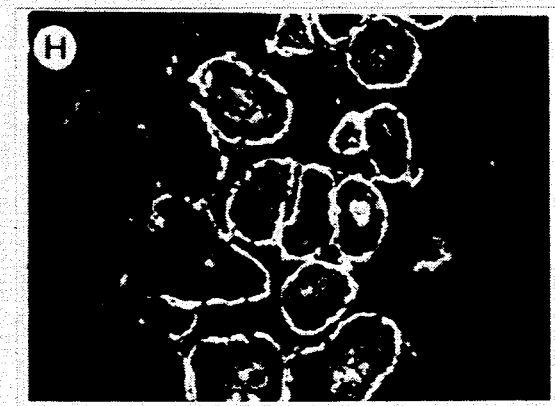

The enzyme reactions were performed as described under "Experimental Procedures" using crude homogenates as enzyme sources.
ND = none detected The results of transfer of $^{14}$C-galactose to Lc$_3$ catalyzed by fractions from normal colonic mucosa and NCI-H69 cells is shown in FIG. 5 and Table 3. A single labelled band which co-migrates with nLc$_4$ is found after transfer by enzyme from NCI-H69 cells (FIG. 5, lane 2). In the case of the normal colonic mucosa, a band that co-migrates with nLc$_4$ is found and in addition a faster migrating band is observed (lane 3). Identification of these bands by immunostain analysis by antibody 1B2 after transfer with unlabelled galactose indicates that the single product formed by NCI-H69 cells and the slower migrating band in the mucosal fraction is nLc$_4$ (FIG. 5, lanes 4 and 6, respectively). This was confirmed by isolating the individual $^{14}$C-labeled bands from each reaction mixture and TLC analysis of each band after acetylation. Results indicate that the single band from NCI-H69 cells and the slower band from the mucosal fractions co-migrate as acetylated derivatives with nLc$_4$. The faster migrating band in the mucosal fractions co-migrates with standard Lc$_4$ as acetylated derivatives (results not shown). The quantitative incorporation of $^{14}$C-galactose into each product is shown in Table 3. Approximately 60 to 65% of the $^{14}$C-galactose transferred to Lc$_3$ is incorporated into nLc$_4$.

The results indicate that normal colonic mucosa has significant activity of both a β1-4galactosyltransferase and an α1-3fucosyltransferase. These enzymes are required for synthesis of type 2 chain core structures and fucosylated derivatives. Despite the level of expression of the α1-3fucosyltransferase, almost all of the type 2 chain structures found in normal colonic mucosa were sialylated derivatives and were not converted to either Le$^x$ or sialyl-Le$^x$ determinant structures. The lack of expression of fucosylated derivatives in the presence of significant fucosyltransferase activity and β1-4galactosyltransferase activity was investigated further as shown in the next example below.

EXAMPLE 4

Tissue Immunofluorescence Studies of Normal Adult Proximal Colon and Fetal Intestine To determine the reason for the lack of expression of large quantities of type 2 chain structures and their fucosylated derivatives in normal mucosa the tissue localization of these carbohydrate structures was studied in normal adult colon tissue and in human fetal colon tissue. Fetal colon tissue has been shown to express type 2 chain fucosylated antigens similar to colonic adenocarcinomas. The expression of these antigens has thus been described as onco-fetal in nature. For this reason, fetal colon tissue is a good comparative tissue to study expression of these carbohydrate antigens in relation to both developmental and oncogenic changes.

Results presented in FIG. 6 indicate the comparative expression of carbohydrate antigens in normal adult proximal colon and in proximal portions of fetal colon tissue. FIGS. 6A and 6B demonstrate the binding of FH3 antibody specific for Le$^x$ antigens (*J. Biol. Chem.*, 259 4681–4685 (1984)) in neuraminidase treated adult and fetal colon tissue, respectively. In agreement with previously reported data (*J. Exp. Med.*, 159, 506–520 (1984)), almost no staining is observed in adult tissue whereas significant staining is observed in crypt cells and the epithelial cell layer of fetal colon tissue. Similar results were obtained with tissue sections without neuraminidase treatment except that the staining intensity of fetal tissue was less indicating the presence of some sialyl-Le$^x$ in this tissue (*Cancer Res.*, 45, 3711–3717 (1985), Cancer Res., 44, 5279–5285 (1984)) (results not shown). FIGS. 6C and 6D show results of tissue staining with antibody specific for type 1 chain based Le$^a$ antigens after treatment with neuraminidase. Intense staining of crypt cells and epithelial cells of both adult and fetal tissue is observed. This is consistent with similar results previously reported (*Lab. Invest.*, 50, 394–400 (1984), *Cancer Res.*, 45, 4499–4511 (1985)) and indicate the presence of a fucosyltransferase associated with synthesis of Le$^a$ structures from type 1 chain precursors in the epithelial cell layer of both fetal and adult proximal colon tissue. FIGS. 6E and 6F show results of staining with antibody specific for type 2 chain structures nLc$_4$, nLc$_6$, etc. prior to neuraminidase treatment of the tissue sections. Essentially no staining of adult epithelial cells was observed. Virtually all staining occurred in the lamina propria of adult mucosa where infiltrative cells are stained (*J. Biol. Chem.*, 260, 1067–1082 (1985), *J. Immunol.*, 134, 2498–2506 (1985)) (FIG. 6E). In contrast, intense staining is observed in the epithelial cell layer of fetal tissue (FIG. 6F). This result is further magnified after neuraminidase treating the tissue sections reflecting the abundance of gangliosides in these cells. Panels G and H show these results. Staining in adult lamina propria is much more intense and is still absent from the layer of epithelial cells (FIG. 6G). Staining of cells of fetal colon is again limited to cells of the epithelium. Thus, the small quantity of type 2 chain structures detected in normal mucosa as described in previous sections is most probably due to contamination of the epithelial cells with leukocytes. These results indicate that type 2 chain structures nLc$_4$, nLc$_6$, etc. are expressed in epithelial cells of fetal colon but not in epithelial cells of adult tissue. Fucosylated derivatives are restricted to epithelial cells. These results strongly suggest that the α1-¾fucosyltransferase activity and synthesis of type 2 core chains are properties of different cell populations of normal colonic mucosa. Oncofetal expression of all type 2 chain based antigens which occur in fetal colonic epithelia and adult colonic adenocarcinomas is most probably due to the retrogenetic expression of type 2 chain core structures which are normally absent in adult colonic epithelial cells.

DISCUSSION

The results presented in Examples 1 to 4 indicate that expression of type 2 chain structures in general and Le$^x$ antigen structures in particular are onco-developmental in nature. This means that these carbohydrate structures are normally expressed during certain stages of normal development, regress greatly in adult tissues, and reappear in association with oncogenesis. Similar results have been obtained from a developmental aspect in mouse embryos where Le$^x$ structures appear during the 8 to 16 cell stage and regress after the 32 cell stage (*Proc. Natl. Acad. Sci. USA*, 75, 5565–5569 (1978). This implies a functional role for this carbohydrate structure during development which is also important during oncogenesis. As a consequence of this, changes in the carbohydrate composition of colon cells may be an early indicator of oncogenesis and thus have diagnostic value. Evidence for this has been obtained for the Le$^y$ determinant which also carries an $\alpha$1-3 linked fucose residue on a type 2 lacto-series chain (*Cancer Res.*, 46, 2639–2644 (1986), *Cancer Res.*, 46, 5985–5992 (1986)). The expression of the Le$^y$ determinant on colonic polyps showing greater dysplasia was noted. This antigen is also common in colonic adenocarcinomas.

The potential functional significance of these types of carbohydrate antigen changes in oncogenesis and the resulting value for diagnosis is clouded by the great diversity of antigens found in actual colonic adenocarcinomas. No single structure or monoclonal antibody generated against a given structure has been shown to be specific for all adenocarcinoma tumors. This has limited the use of these antigens and antibodies against these structures in diagnostic applications. Therefore, it is of considerable importance to determine the specific enzymatic lesion or lesions which are responsible for the formation of these antigens in premalignant tissues and tumors and base diagnostic procedures on a more common expression or mechanism of activation of antigen expression. In order to determine this, information has been gained to isolate this lesion or lesions. As indicated in Examples 1 to 4, alteration of expression of an $\alpha$1-3fucosyltransferase does not correlate with fucosylated type 2 lacto-series chain expression. In fact, this activity in normal mucosa is associated with a fucosyltransferase with dual specificity as an $\alpha$1-3/4fucosyltransferase which can transfer fucose to either type 1 or 2 lacto-series chains. This enzyme is associated with the expression of the Le gene of the Lewis blood group. This is found to be normally expressed in secretory tissues of man, although the extent of accumulation of chemical quantities of these structures is low compared to tumor tissues.

Also shown in Examples 1 to 4 are results which indicate that type 2 lacto-series core chains are not found in epithelial cells of normal adult colonic mucosa although fucosyltransferase activity is expressed in these cells. Type 2 lacto-series core chains were found in fetal colonic epithelial cells. This indicates that expression of type 2 chain based antigens in adenocarcinomas is regulated through activation of synthesis of type 2 chain core structures in epithelial cells of colonic mucosa. The specific enzymatic lesion associated with activation of type 2 lacto-series core chain synthesis in colonic epithelial cells was investigated and is described in the next series of Examples.

SECOND SERIES OF EXAMPLES

To determine the specific enzymatic lesion responsible for the regulation of synthesis-of type 2 lacto-series core chains, a series of investigations were performed using tissue culture cell lines of normal adult colonic mucosal epithelial cell origin and several human colonic adenocarcinoma cell lines. Using these cell lines comparative aspects of the normal cells and tumor cells can be obtained without contamination from other cell types as with scraped colonic mucosa.

EXAMPLE 5

Analysis of Glycolipids Isolated from Normal Mucosal and Colonic Adenocarcinoma Cell Lines To determine the nature of carbohydrate structures on glycolipids of normal colonic epithelial cells and adenocarcinomas from cell lines in comparison with results presented in Example 1 above, the following studies were undertaken.

FIG. 7 shows results of glycolipid analysis by orcinol staining and TLC immunostain analysis. It is apparent by orcinol staining that only the transformed cell lines contain significant quantities of slower migrating, long chain glycolipid bands (FIG. 7A, lanes 7–14). The normal mucosal epithelial cell line, HCMC, contain almost no longer chain glycolipids, the major bands co-migrating with Gb$_3$ and Gb$_4$ (lane 6). These results are equivalent to those obtained with glycolipids extracted from colonic adenocarcinoma tumors (*J. Biol. Chem.*, 259, 4672–4680 (1984)).

Figure 7A:
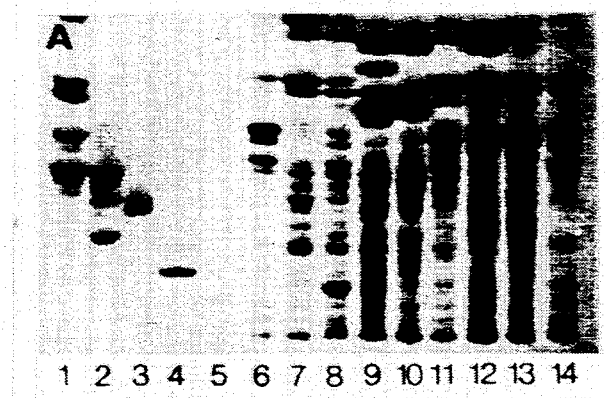
FIG. 7A Orcinol staining. Lane 1, standard globoside (Gb4), Gb3, and lactosylceramide (in terms of increasing mobility); lane 2, standard nLc6 and nLc4 (in terms of increasing mobility); lane 3, standard III$^3$-FucnLc4; lane 4, standard V$^3$FucnLc6; lane 5, standard III$^3$V$^3$Fuc$_2$nLc6; lanes 6–14, neutral glycolipids from HCMC, DLD-1, HCT-15, Colo 205, SW403, SW480, SW948, SW1417, and PC9 cells, respectively. Panel B: Immunostain with 1B2 antibody. Lane 1, human type "O" whole blood cell neutral glycolipid fraction; lanes 2–10, neutral glycolipids from cell lines as described in FIG. 7A.
Figure 7B:
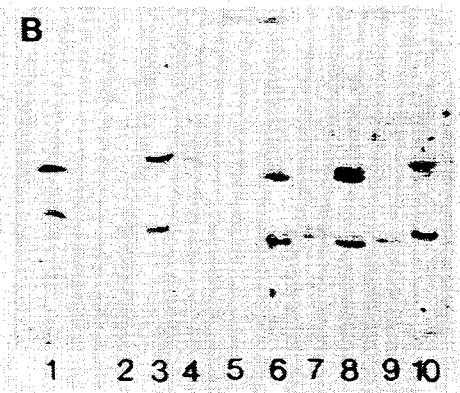
FIG. 7 is a high performance thin layer chromatography analysis showing that neutral glycolipids from normal human colonic epithelial cells contain almost no detectable type 1 or 2 chain based glycolipid antigens but that several colonic adenocarcinoma cell lines contain large quantities of these structures based on orcinol (FIG. 7A) or immunostain analysis with specific antibodies (FIGS. 7B–7G). Neutral glycolipids are isolated from normal colon and colonic adenocarcinoma cell lines.
FIG. 7C: Immunostain with AH6 antibody. Lanes 1–10 are as described for FIG. 7B.
FIG. 7D Immunostain with anti-Le$^a$ antibody. Lanes 1–10 are as described for FIG. 7B. The solvent system was composed of $CHCl_3:CH_3OH:H_2O$, 60:35:8.
Figure 7C:
Figure 7D:
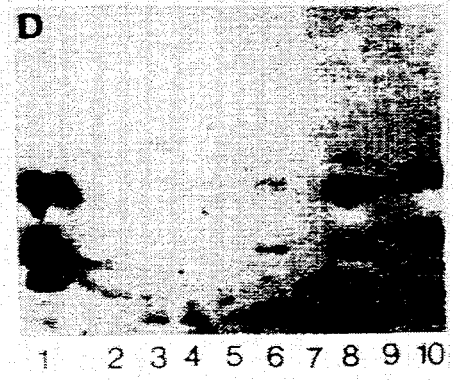
Figure 7E:
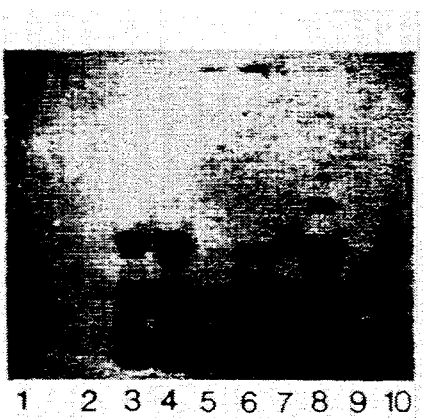
Figure 7F:
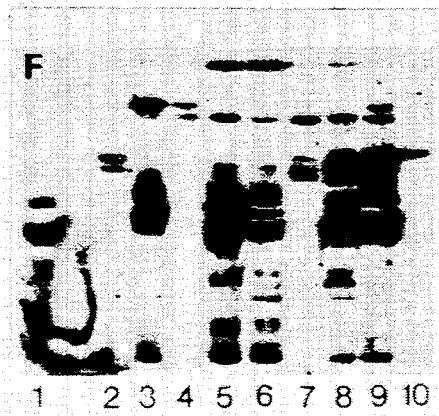
Figure 7G:
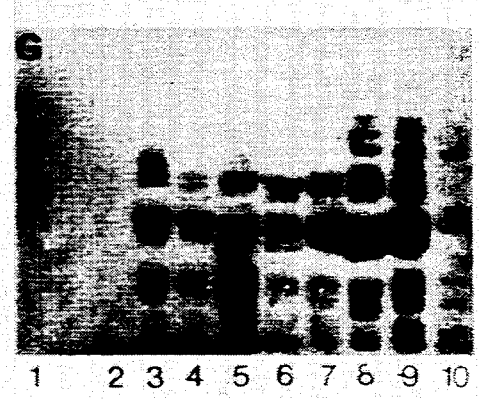

The nature of the glycolipids found in these cells was further studied by TLC immunostain analysis. FIG. 7B shows results with the type 2 chain N-acetyllactosaminyl residue specific antibody 1B2. Staining of bands co-migrating with nLc$_4$ and/or nLc$_6$ is observed in each of the adenocarcinoma cell lines (lanes 3–10), although weak staining is found with Colo 205 cells. Weak staining is also observed with HCMC cells where only nLc$_6$ is detectable. Type 2 core chains are the biosynthetic intermediate for a variety of fucosylated derivatives. One of these is the Le$^y$ structure. Immunostain analysis with the Le$^y$ specific antibody AH6 is shown in FIG. 7C. Staining is absent in neutral glycolipids from HCMC cells, weak in Colo 205 cells, and very strong in each of the other adenocarcinoma cell lines and PC9 cells. Both short and long chain derivatives are found indicating the accumulation of Le$^y$ structures in adenocarcinomas but not in normal cells. FIG. 7D shows results of immunostain with an antibody specific for the type 1 chain based Le$^a$ structure. Weak staining of a band co-migrating with III$^4$FucLc$_4$ is found in HCMC cells and some of the adenocarcinoma cell lines. Intense staining is observed with most of the adenocarcinoma cell lines, A more complete summary of TLC immunostain results is shown in Table 5 using a variety of monoclonal antibodies whose specificities are described in Table 4, These results indicate that both neutral glycolipids and gangliosides based on type 1 and 2 lacto-series chains accumulate in colonic adenocarcinoma cell lines and these structures are either weak or not expressed in normal mucosal epithelial cells.

TABLE 4

| Antibodies Used in This Study | | |
|---|---|---|
| Antibody | Specificity | ATCC Number |
| 2D4 | asialo GM$_2$ | TIB 185 |
| 38.13 | Gb$_3$ structure | |
| J1 | Lc$_3$ structure | |
| 1B2 | type 2 chain lacto series | TIB 189 |
| BE2 | H antigens on type 2 chains | TIB 182 |
| H1B4 | H antigens on types 1 & 2 chains | |
| Lewis a | Le$^a$ structure | CRL 1670 |

TABLE 4-continued

| Antibodies Used in This Study | | |
|---|---|---|
| Antibody | Specificity | ATCC Number |
| Lewis b | $Le^b$ structure | HB 8326 |
| 1116-NS-19-9 | sialyl $Le^a$ | HB 8059 |
| WGHS-29-1 | $Le^x$ structure | |
| AH6 | $Le^y$ structure | |
| FH6 | sialyl $Le^x$ | |

EXAMPLE 6

Pathway of Synthesis of Type 1 and 2 Chain Based Glycolipid Antigens in Normal Colonic Epithelial and Colonic Adenocarcinoma Cell Lines In order to isolate the specific enzymatic lesion associated with the expression of tacto-series antigens in adenocarcinomas but not in normal colonic epithelial cells, the activities of several enzymes involved in the synthesis of these antigens were determined and compared between normal epithelial and adenocarcinoma cells.

The pathway of synthesis and specific activity of the enzyme catalyzing each step in normal colonic epithelial and colonic adenocarcinoma cell lines is shown in Table 6. For the purposes of comparison between cell lines, results are reported as specific activities in crude cell homogenates.

TABLE 5

Summary of TLC Immunostain Results with Neutral Glycolipids and Gangliosides Isolated from Normal Colonic Mucosal and Colonic Adenocarcinoma Cell Lines

| | Glycolipid Presence or Absence | | | | | | | | | | | |
|---|---|---|---|---|---|---|---|---|---|---|---|---|
| | | | | Type 2 | | | H Antigens | | | | Sialyl | Sialyl |
| Cell Line | $Gb_3$ | $Lc_3$ | $Gq_3$ | Chain | $Le^x$ | $Le^y$ | Types 1 & 2 | Type 2 | $Le^a$ | $Le^b$ | $Le^x$ | $Le^a$ |
| HCMC (O)$^a$ | ++ | − | − | +$^{c,d}$ | − | − | +$^d$ | − | +$^d$ | − | − | − |
| DLD-1 (O) | − | − | − | ++ | +$^d$ | ++ | + | + | +++ | ++ | − | +++ |
| HCT-15 (O) | + | − | − | + | +$^d$ | ++ | ++ | + | +$^d$ | + | − | − |
| Colo 205 (O)$^b$ | + | − | − | +$^d$ | − | +$^d$ | +++ | +$^d$ | +++ | +++ | − | +++ |
| SW403 (O) | +$^d$ | − | − | + | + | ++ | +++ | + | ++ | + | − | +$^d$ |
| SW480 (A) | ++ | − | − | +$^c$ | +$^e$ | ++ | +++ | + | +$^d$ | + | − | +$^d$ |
| SW948 (O) | ++ | − | − | + | ++ | ++ | ++ | + | ++ | +++ | + | +++ |
| SW1417 (B) | ++ | − | − | +$^c$ | − | + | ++ | − | ++ | +++ | − | +++ |
| PC9 (O)$^b$ | + | − | − | + | ++ | ++ | + | + | − | − | + | − |

The presence or absence of bands staining with appropriate antibodies is given. −, not detected; +, detectable but may be weak; ++, moderate staining; +++, strong staining
$^a$blood type of donor individual; $^b$blood type of donor individual deduced from TLC immunostain results (i.e., negative with monoclonal antibodies against A or B structure); $^c$mainly nLc$_6$ staining; $^d$very weak staining; $^e$mainly III$^e$V$^e$Fuc$_2$nLc$_6$ staining
The procedures used are as described under "Experimental Procedures" using antibodies shown in Table 4.

These results indicate that similar glycolipid profiles and lack of significant quantities of lacto-series antigens are shared with both normal colonic mucosa and the colonic epithelial cell line. In addition, both adenocarcinoma tumors and cell lines have accumulations of a diversity of both type 1 and 2 chain based carbohydrate antigens.

TABLE 6

Pathway of Synthesis of Lacto-Series Antigens and Specific Activity of Associated Glycosyltransferases in Crude Homogenates of Normal Colonic Mucosal and Colonic Adenocarcinoma Cell Lines Glc$\beta$1-1Cer
(glucosylceramide)

$\beta$1-4Galactosyltransferase
Reaction 1 ↓

Gb$_3$ ← Gal$\beta$1-4Glc$\beta$1-1Cer → GM$_3$
(lactosylceramide)

$\beta$1-3N-acetylglucosaminyltransferase
Reation 2 ↓

GlcNAc$\beta$1-3Gal$\beta$1-4Glc$\beta$1-1Cer $\beta$1-3Galactosyltransferase     $\beta$1-4Galactosyltransferase
Reaction 3    (Lc$_3$)    Reaction 4

Gal$\beta$1-3GlcNAc$\beta$1-3Gal$\beta$1-1Cer     Gal$\beta$1-4GlcNAc$\beta$1-3Gal$\beta$1-4Glc$\beta$1-1Cer
$\alpha$1-4Fucosyl- (Lc$_4$)           (nLc$_4$)   $\alpha$1-3Fucosyl-
transferase                                     transferase
Reaction 5 ↓                                    Reaction 6 ↓

Gal$\beta$1-3GlcNAc$\beta$1-3Gal$\beta$1-4Glc$\beta$1-1Cer     Gal$\beta$1-4GlcNAc$\beta$1-3Gal$\beta$1-4Glc$\beta$1-1Cer
          4                                           3
          |          (Le$^a$)                         |         (Le$^x$)
       Fuc$\alpha$1                                Fuc$\alpha$1

| | Reaction (pmol/hr/mg protein) | | | | | |
|---|---|---|---|---|---|---|
| Cell Line | 1 | 2 | 3 | 4 | 5 | 6 |
| HCMC | 245. | ND | ND | 1139. | 12. | 73. |
| DLD-1 | 498. | 22. | 59. | 908. | 38. | 144. |
| HCT-15 | 471. | 252. | ND | 596. | 40. | 136. |
| Colo 205 | 722. | 93. | 2170. | 1870. | 149. | 64. |

TABLE 6-continued

| | | | | | | |
|---|---|---|---|---|---|---|
| SW 403 | 1598. | 165. | 651. | 1881. | 52. | 190. |
| SW 480 | 81. | 51. | 34. | 156. | 15. | 91. |
| SW 948 | 337. | 68. | 51. | 525. | 43. | 80. |
| SW 1417 | 523. | 106. | 244. | 733. | 25. | 92. |
| H69 | 80. | 123. | ND | 888. | ND | 174. |
| PC9 | 707. | 297. | ND | 1416. | ND | 272. |

The reaction mixtures were as described below under "Experimental Procedures"
ND = non detected The initial reaction involves synthesis of lactosylceramide from the precursor glucosylceramide catalyzed by $\beta$1-4galactosyltransferase. This activity is variable but is highly expressed in normal mucosal cells and in all adenocarcinoma cell lines tested. Lactosylceramide is a common precursor for a variety of competing glycosyltransferases as shown. One fate of lactosylceramide is lacto-series chain synthesis catalyzed by $\beta$1→3N-acetylglucosaminyltransferase to form the product Lc$_3$ (reaction 2). This activity was also variable but found in all transformed cell lines tested, however no activity was detected in the normal epithelial HCMC cells. No detectable hydrolysis of [$^{14}$C]-GlcNAc labelled Lc$_3$ by endogenous $\beta$-N-acetylglucosaminidase was found for any of the cell lines tested over a 2 hour incubation period indicating that the observed differences in $\beta$1→3N-acetylglucosaminyltransferase activity reflects altered biosynthesis rather than degradation (results not shown).

Figure 8:
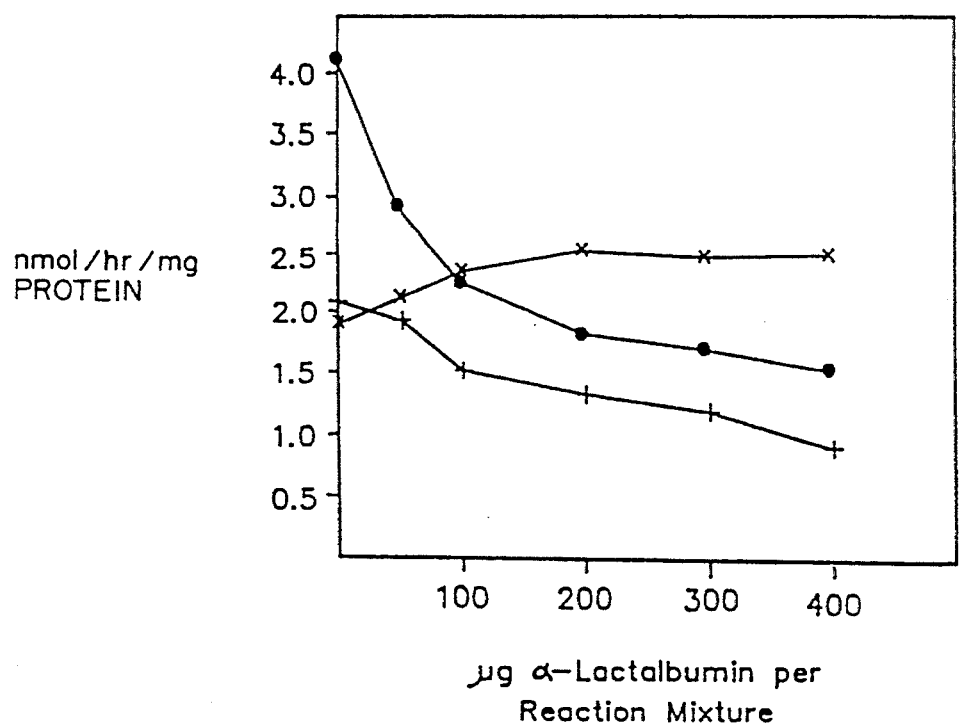
FIG. 8 shows that $\beta$1-4galactosyltransferase expressed in colon cells and associated with synthesis of type 2 chain precursor structures is also responsible for the synthesis of lactosylceramide which is common to all cells both normal and transformed and is similar to the lactose synthetase A protein. The effect of increasing $\alpha$-lactalbumin on the transfer of galactose to glucosylceramide, +—+, Lc3 forming nLc4, o—o, and Lc3 forming Lc4, x—x, catalyzed by a 0.2% Triton X-100 soluble fraction from SW403 cells is shown. The assays were conducted in the presence of 30 $\mu$g of the indicated acceptor and 0.2 mg of solubilized protein.

Synthesis of type 1 and 2 chain structures Lc$_4$ and nLc$_4$ are catalyzed by $\beta$1-3 and $\beta$1-4galactosyltransferases, respectively, competing for Lc$_3$. A $\beta$1-4-galactosyltransferase responsible for transfer of Gal to Lc$_3$ in human plasma was previously reported to be lactose synthetase A protein which was also involved in the synthesis of lactosylceramide (J. Biochem., 92, 1123-1127 (1982)). This was confirmed in adenocarcinoma cells as shown in FIG. 8. The effect of increasing $\alpha$-lactalbumin on the $\beta$1-4galactosyltransferase activity in SW403 cells is seen with glucosylceramide and Lc$_3$ as acceptors. A similar decrease in transfer to each acceptor with increasing $\alpha$-lactalbumin concentration was observed indicating that this membrane bound enzyme is similar to lactose synthetase A protein. Slight activation of $\beta$1-3galactosyltransferase with Lc$_3$ as acceptor was found due presumably to the reduced substrate competition with the inhibited $\beta$1-4galactosyltransferase.

Formation of fucosylated derivatives of type 1 and 2 chains generated in the previous reactions are catalyzed by either $\alpha$1-3 or $\alpha$1-4 fucosyltransferase activities. Significant but variable amounts of both activities were found in normal mucosal and adenocarcinoma cell lines. In contrast, the lung carcinoma cell lines tested contained only $\alpha$1-3 specific fucosyltransferase. Multiple fucosyltransferases have been described in human tissues, ie. both $\alpha$1-3 specific (J. Biol. Chem., 260, 7619-7627 (1985), Eur. J. Biochem., 30, 269-277 (1972), Eur. J. Biochem., 130, 347-351 (1983)) and $\alpha$1-$\frac{3}{4}$ specific (J. Biol. Chem., 256, 10456-10463 (1981), Biochem. Biophys. Res. Commun., 100, 1611-1618 (1981), FEBS Lett., 142, 77-80 (1982)) fucosyltransferases, the latter being associated with Le-gene expression. The nature of these activities in colon derived cells was tested by kinetic studies to gain information whether single or multiple enzymes are present which catalyze transfer of fucose in $\alpha$1-3 and/or $\alpha$1-4 linkages. These results are shown in Table 7.

TABLE 7

Substrate competition studies with fucosyltransferase from homogenates of normal colonic mucosa, colonic adenocarcinoma, and small cell lung carcinoma cells.

| | pmol [$^{14}$C]fucose transferred/hr/mg protein to: | | | | |
|---|---|---|---|---|---|
| Enzyme Source | Lc$_4$ | nLc$_4$ | Lc$_4$ + nLc$_4$ | One enzyme | Two enzymes |
| HCMC | 11. | 74. | 48. | 40. | 85. |
| DLD-1 | 38. | 144. | 115. | 87. | 182. |
| HCT-15 | 40. | 136. | 93. | 84. | 176. |
| SW 480 | 15. | 91. | 77. | 50. | 106. |
| SW 948 | 43. | 80. | 82. | 56. | 123. |
| SW 1417 | 25. | 92. | 73. | 56. | 117. |
| NCI-H69 | ND | 174. | 163. | | |

Reaction mixtures were as described under "Experimental Procedures" and contained 40 µg of Lc$_4$, nLc$_4$, or 40 µg of both Lc$_4$ and nLc$_4$. Calculated values for activity with mixed acceptor composition were determined using the following equations.

Two enzymes $v_t = v_a + v_b$

One enzyme $v_t = \dfrac{V_a\, a/K_a + V_b\, b/K_b}{1 + a/K_a + b/K_b}$

ND = none detected

Assays containing both Lc$_4$ and nLc$_4$ yielded total transfer of $^{14}$C-fucose in excess of that predicted if a single enzyme were present, This is most probably due to the presence of some H-gene and/or Se-gene $\alpha$1-2fucosyltransferase in these cells, the products of which are not resolved on TLC from $\alpha$1-3 and $\alpha$1-4 fucosyl products. Transfer of fucose to Lc$_4$ and nLc$_4$ when mixed with a non-fucosyl acceptor such as Gb$_4$ yielded the same activity as when they were assayed alone indicating that mixing acceptors does not in itself lower the resulting activity (results not shown). These results suggest that although formation of $\alpha$1-2 fucosyl products may occur, and since the activity with mixed acceptors is far from additive compared to the acceptors by themselves, the most probable conclusion is the presence of an enzyme capable of transferring fucose in either $\alpha$1-3 or $\alpha$1-4 linkages in colonic mucosal and adenocarcinoma cells. Thus, the finding of type 2 chain fucosylated antigens in human colonic adenocarcinoma cells and tumors is most probably also associated with Le-gene expression as has been previously reported for expression of Lewis antigens (Lancet, 1332-1333 (1982)).

Figure 9:
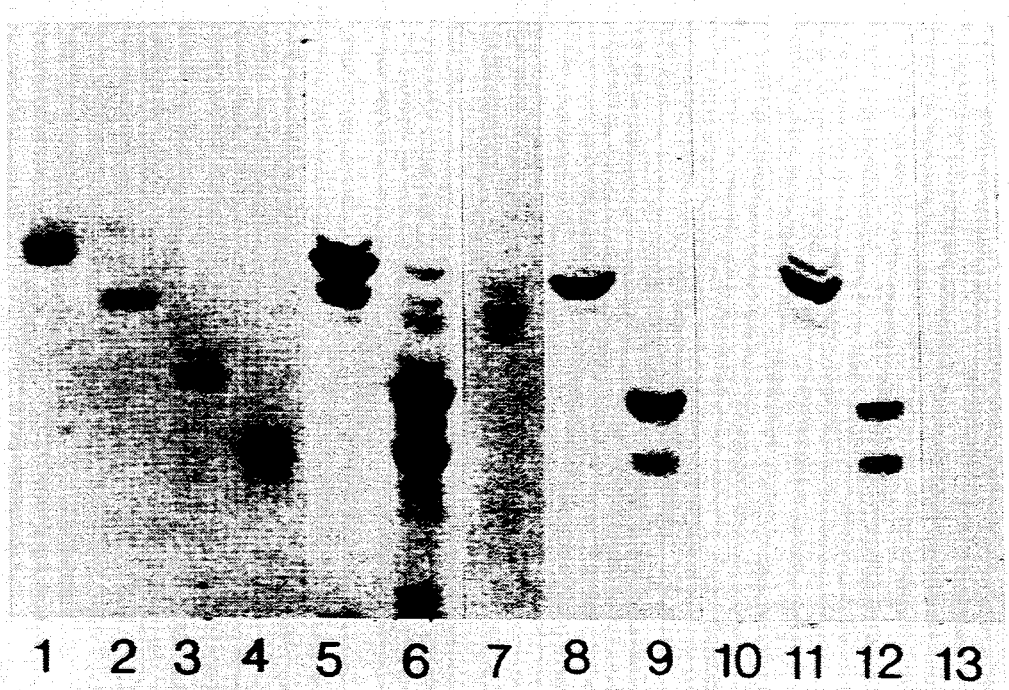
FIG. 9 presents thin layer chromatography profiles showing that the fucosyltransferase activity from normal colonic epithelial cells is similar to that from adenocarcinoma cells. Lane 1, standard III$^3$FucnLc4; lane 2, standard nLc6; lane 3, standard V$^3$FucnLc6; lane 4, standard III$^3$V$^3$Fuc$_2$nLc6; lanes 5, 6, and 7, autoradiographs of $^{14}$C-labeled products from NCI-H69 cells with nLc4, nLc6, and endogenous acceptors, respectively; lanes 8, 9, and 10, $^{14}$C-labeled products from HCMC cells with nLc4, nLc6, and endogenous acceptors, respectively; lanes 11,12, and 1.3, $^{14}$C-labeled products from SW948 cells with nLc4, nLc6, and endogenous acceptors, respectively. The solvent system was composed of $CHCl_3:CH_3OH:H_2O$ (60:35:8). Standard glycolipids were visualized by orcinol spray.
Figure 10A:
FIG. 10A: Immunofluorescence of normal mucosa after pre-incubation with Lc3.
Figure 10B:
FIG. 10B: Immunofluorescence of normal mucosa after incubation with a reaction mixture containing UDPGal.
Figure 10C:
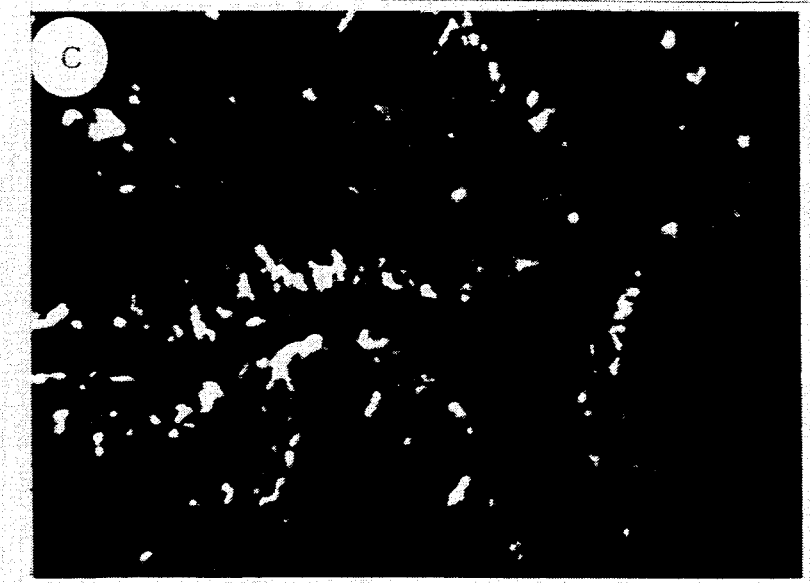
FIG. 10C: Immunofluorescence of normal mucosa after pre-incubation with Lc3 and incubation with a reaction mixture containing UDPGal.
Figure 10D:
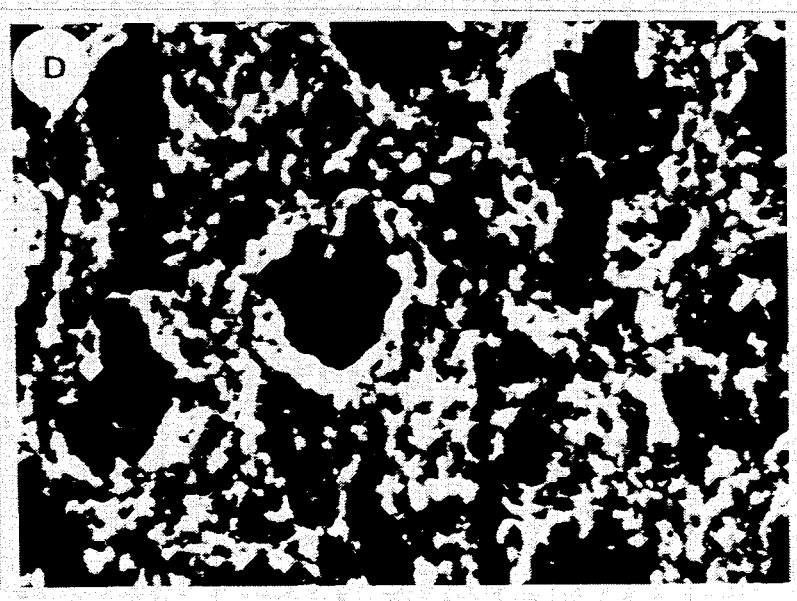
FIG. 10D: Immunofluorescence of normal mucosa after pre-incubation with nLc4. The sections were treated as described under "Experimental Procedures". Magnification 400 x.

The products formed by transfer of fucose to different type 2 chain acceptors catalyzed by the $\alpha$1-$\frac{3}{4}$ specific enzyme from normal mucosal and adenocarcinoma cells were compared to those catalyzed by the $\alpha$1-3 specific enzyme from NCI-H69 cells and is shown in FIG. 9. For each enzyme from either normal or transformed cells the same pattern of reaction products was observed. In particular, the $\alpha$1-$\frac{3}{4}$ specific enzyme from normal colonic mucosal HCMC cells and from the colonic adenocarcinoma cell line yielded a single Le$^x$ reactive band from nLc$_4$ and two products that were Le$^x$ reactive from transfer to nLc$_6$ which co-migrated with V$^3$FucnLc$_6$ and III$^3$V$^3$Fuc$_2$nLc$_6$. Synthesis of polyfucosyl structures is in common with results shown here and previously reported for the $\alpha$1-3 specific enzyme (*J. Biol. Chem.*, 260, 7619–7627 (1985)) and with results from structural studies with colonic adenocarcinoma tumors (*J. Biol. Chem.*, 259, 4672–4680 (1984)).

These results indicate that cell lines from normal colonic epithelium and adenocarcinomas behaved very similarly as normal mucosa and adenocarcinoma tumors in terms of expression of glycolipid antigens and enzymes involved in the synthesis. The most significant finding is that expression of both type 1 and 2 chain based lacto-series antigens is correlated with the expression in adenocarcinomas of a B1→3N-acetylglucosaminyltransferase which is not found in normal colonic epithelial cells. The alteration in the activity of this enzyme is the specific enzymatic lesion associated with the production of the entire series of both type 1 and 2 chain based lacto-series antigens in adenocarcinomas.

EXAMPLE 7 in situ Biosynthesis of Type 2 Chain Structures in Epithelial Cells of Normal Human Colonic Mucosa In order to confirm the above conclusion that alteration of a $\beta1\rightarrow3$N-acetylglucosaminyltransferase is the enzymatic lesion responsible for the occurrence of lacto-series based antigens in adenocarcinomas, the following experiment was performed. Freshly obtained normal adult colonic tissue was obtained and cryostat sectioned. A solution containing the product of the proposed missing enzyme, Lc$_3$, was layered over the tissue sections. Glycolipids under this condition will be absorbed by the cell membranes of the tissue. Once the Lc$_3$ is absorbed by the membranes, a reaction mixture containing UDPGalis incubated with the sections, and the presence of the type 2 chain product nLc$_4$ is detected by a monoclonal antibody (1B2) specific for type 2 chain core structures. The ability of normal colonic epithelial cells to catalyze the synthesis of nLc$_4$ would support the notion that synthesis of its immediate precursor is limiting in normal colon epithelial cells.

Demonstration of in situ biosynthesized nLc$_4$ from added Lc$_3$ in normal adult proximal colon epithelial cells using the procedures described in Methods is shown in FIG. 10. This figure indicates that sections of normal colonic mucosa contain almost no detectable N-acetyllactosaminyl residues based on antibody 1B2 binding after pre-incubation of the sections with Lc$_3$ in PBS (FIG. 10A). Incubation of sections in the absence of Lc$_3$ pre-incubation with a reaction mixture containing UDPGal had no effect on the nature of antibody binding (FIG. 10B). However, pre-incubation of the sections with Lc$_3$ in PBS for 4 hours prior to incubation with UDPGal containing reaction mixtures yielded a product which was detected by binding of antibody 1B2 (FIG. 10C). The adsorption of Lc$_3$ by the membranes and Subsequent transfer of $\beta$1-4 linked galactose was highest and easily detectable in the epithelial cells of the normal mucosa. FIG. 10D shows binding of antibody 1B2 to sections which were pre-incubated in the presence of nLc$_4$. A more generalized staining by the antibody is observed. Pre-incubation of tissue sections with irrelevant glycolipids yielded no antibody binding (results not shown). These results indicate that Lc$_3$ exogenously added to normal mucosa tissue sections can be incorporated into the membranes of colonic epithelial cells and in the presence of UDPGal, an epithelial cell derived $\beta$1-4galactosyltransferase catalyzes the formation of nLc$_4$. These results further indicate that the enzymatic activity responsible for appearance of lacto-series antigens during development and in association with oncogenesis is a $\beta1\rightarrow3$N-acetylglucosaminyltransferase which is responsible for synthesis of Lc$_3$.

EXAMPLE 8

Pattern of Expression of Glycosyltransferase Activities in Normal Colonic Mucosa and Colonic Adenocarcinoma Tumors The specific activities of glycosyltransferases associated with synthesis of lacto-series glycolipids is compared as crude tissue homogenates from several samples of scraped normal colonic mucosa and colonic adenocarcinoma tumors as shown in Table 8.

TABLE 8

Specific Activity of Glycosyltransferase Activities Associated with Synthesis of Type 2 Lacto-Series Antigens in Crude Homogenates of Normal Human Colonic Mucosa and Colonic Adenocarcinoma Tumors.

| Enzyme Source | $\beta$1-3GlcNAc transferase pmol/hr/ mg protein | $\beta$1-4Gal transferase pmol/hr/ mg protein | $\alpha$1-3Fuc transferase pmol/hr/ mg protein |
|---|---|---|---|
| Normal mucosa case #1 | 18. | 459. | 167. |
| Normal mucosa case #2 | 25. | 772. | 299. |
| Normal mucosa case #3 | 18. | 445. | 100. |
| Adenocarcinoma case 277-1 | 133. | 853. | 60. |
| Adenocarcinoma case 297-1 | 276. | 1285. | 20. |
| Adenocarcinoma case 464-1 | 100. | 677. | 20. |

The reaction mixtures were as described under "Experimental Procedures".

The specific activity of $\beta1\rightarrow3$N-acetylglucosaminyltransferase is increased 6- to 11-fold in homogenates of colonic adenocarcinoma tumors compared to scraped normal adult colonic mucosa. The activities of $\beta$1-4galactosyltransferase and $\alpha$1-3fucosyltransferase associated with synthesis of Le$^x$ determinant structures from the immediate precursor Lc$_3$ were found in all tissue samples although the fucosyltransferase was generally lower in the tumors. The reason for this is unclear and may relate to decreased relative stability of the fucosyltransferase compared to the other enzymes in the tumors as glycolipids extracted from these tumors contained abundant accumulations of fucosylated glycolipids characteristic of colonic adenocarcinomas (results not shown). The scraped mucosa used in these experiments is not a uniform population of epithelial cells but contains in addition cells of connective tissue and infiltrative cells such as leukocytes. Results shown in Examples 1 to 4 indicated that type 2 lacto-series core chains containing $\beta$1-3 linked GlcNAc residues are not expressed in the epithelial cells of normal adult mucosa. This low $\beta1\rightarrow3$N-acetylglucosaminyl transferase activity detected in scraped normal mucosa is most probably from non-epithelial cells.

These results indicate that significant increases in $\beta1\rightarrow3$N-acetylglucosaminyltransferase are characteristic of colonic adenocarcinomas relative to normal mucosa indicating further the critical nature of the enhancement of this activity during oncogenesis in this tissue. In addition, these clear differences indicate potential for monitoring of this activity or action of the enzyme for diagnostic or prognostic purposes.

DISCUSSION

The results described in Examples 1 to 4 indicated that control of expression of type 2 chain based tumor-associated antigens in normal mucosal epithelial cells and adenocarcinoma tumors was mediated through expression of core chain synthesis in epithelial cells. The results from Examples 5 to 8 extend this to indicate that activation of a β1→3N-acetylglucosaminyltransferase is the enzymatic lesion responsible for formation of all lacto-series tumor-associated antigens found in adenocarcinomas. This enzyme is not detectable in normal colonic epithelial cells. Furthermore, when normal colon tissue is supplemented with the reaction product, type 2 chain structures are synthesized. The data presented also indicates that all of the adenocarcinoma cell lines tested expressed this activity and that its expression correlated with the finding of a wide diversity of carbohydrate structures based on both type 1 and 2 lacto-series core chains. A variety of other enzymes associated with tumor marker synthesis were analyzed. These included β1-4galactosyltransferase which is involved in the synthesis of lactosylceramide or nLc4, β1-3gal-actosyltransferase involved in the synthesis of Lc4, and α1-¾ fucosyltransferase which catalyzes the synthesis of Le$^a$ and Le$^x$ antigens. In each case, none of these activities correlated with the finding of lacto-series antigens in tumor cells and tissues but were absent in normal epithelial cells. Reports in the literature indicate an extremely wide variety of glycolipid structures based on either type 1 or 2 lacto-series chains have been found in adenocarcinomas and defined as tumor associated. A variety of competing transferases can yield a diversity of end-stage products. Depending upon the specific nature of other activities capable of modifying lacto-series chain structures in specific cell populations of colon tumors, many extended derivatives such as Le$^x$ and polyfucosyl Le$^x$ (Biochem. Biophys. Res. Commun., 109, 36–44 (1982), J. Biol. Chem., 259, 4672–4680 (1984)), sialyl Le$^x$ (J. Biol. Chem., 259, 10511–10517 (1984)), Le$^y$ (J. Biol. Chem., 258; 11793–11797 (1983)), or trifucosyl Le$^y$ (J. Biol. Chem., 261, 11247–11253 (1986)) have been found. Thus, although a variety of derivatives are present, the same enzymatic alteration is responsible for their expression and so, they are essentially equivalent with respect to their potential for markers of this process. The presence of large quantities of these antigens in colon tumors tend to obscure the nature of the specific enzyme alteration which leads to their synthesis.

Activation of a β1→3N-acetylglucosaminyltransferase in association with oncogenesis has been shown to be responsible for tumor marker expression. As a result expression of both type 1 and 2 chain based antigens is controlled by the same enzymatic lesion. An apparent paradox is the previous finding of type 1 chain based Le$^a$ antigens in normal mucosal epithelial cells and tissues. This appears to be due to the greater avidity of antibodies specific for type 1 chain structures compared to those specific for type 2 chain structures. Thus, a very low activity of the β1→3N-acetylglucosaminyltransferase which is undetectable in enzyme assays is most probably found in colonic epithelial cells which is responsible for the formation of only immunologically detectable quantities of these structures. In any case, as a consequence, of activation of this enzyme, both type 1 and 2 chain based antigens are formed in association with oncogenesis. Therefore, alteration in expression of this activity should have a more comprehensive marker for this process and have greater diagnostic or prognostic potential.

THIRD SERIES OF EXAMPLES

The nature of the β1→3N-acetylglucosaminyltransferase induced in colonic adenocarcinoma cell lines and absent in normal colonic epithelial cells was characterized in terms of its properties and discussed in this third series of Examples.

EXAMPLE 9

Solubilization of
β1→3N-acetylglucosaminyltransferase from SW403
Cells

To study the β1→3N-acetylglucosaminyltransferase associated with tumor marker synthesis the enzyme was solubilized from tumor cells and characterized.

The β1→3N-acetylglucosaminyltransferase activity to lactosylceramide was solubilized from a 27,000 x g membrane pellet of SW403 cells by 0.2% Triton X-100, The majority of the activity was obtained in the 100,000 x g supernatant fraction. The recovery of the β1→3N-acetylglucosaminyltransferase activity in this fraction was 74% compared to the crude homogenate.

Characterization of the
β1→3N-acetylglucosaminyltransferase

Effect of Detergent and pH on Activity

The effect of various detergents on transfer of GlcNAc to lactosylceramide catalyzed by the solubilized enzyme from SW403 cells was tested and shown in Table 9. The results indicate that a variety of detergents whether non-ionic or ionic stimulate the reaction. The condition which yields the highest activity involves assay in the presence of added Triton CF-54 at a final concentration of 0.3%. The result reported for no additional detergents reflects the effect of a final concentration of Triton X-100 of 0.05% which was added along with the solubilized enzyme.

TABLE 9

| Effect of detergents on β1-3N-acetyl-glucosaminyltransferase activity | |
|---|---|
| Detergent | pmol/hr/mg protein |
| None$^a$ | 14.8 |
| Triton X-100 | 67.9 |
| Triton CF-54 | 80.1 |
| Deoxycholate | 67.5 |
| G-3634-A | 50.5 |
| CHAPSO | 54.5 |

The reaction mixtures were as described below under "Experimental Procedures". Detergents were added at a final concentration of 0.3%.
$^a$A final concentration of Triton X-100 of 0.05% was added to each reaction mixture along with the detergent solubilized enzyme.

Figure 11:
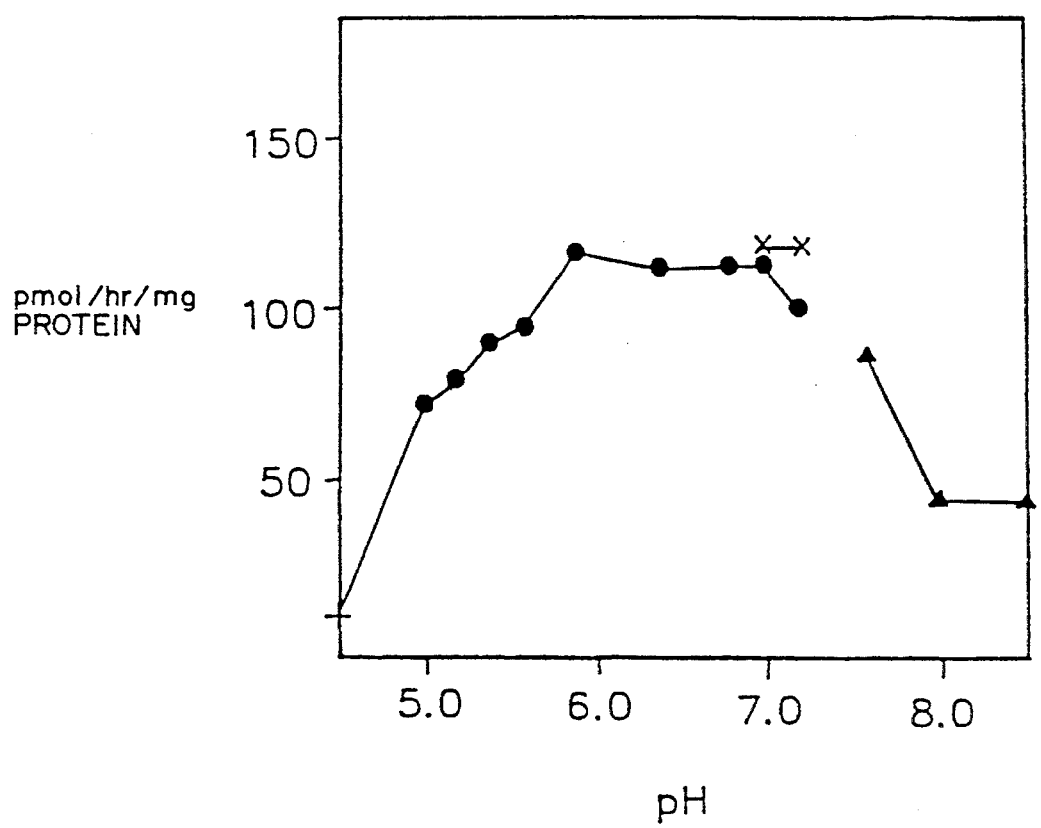
FIG. 11 shows the effect of pH on $\beta$1→3N-acetylglucosaminyltransferase activity. The buffers used are acetate, +—+, cacodylate, o—o, HEPES, x—x, and Tris-HCl.

The pH dependence of the enzyme was studied with a variety of buffers present at 50 mM final concentration at pH values varying from 4.5 to 8.5. These results are shown in FIG. 11. The enzyme was most active over a broad. pH range from 5.8 to 7.5. The highest activity, however, was obtained with HEPES buffer at pH values from 7.0 to 7.2.

Requirements of
β1→3N-acetylglucosaminyltransferase for Optimal
Activity

Transfer of GlcNAc to lactosylceramide was tested under a variety of conditions as shown in Table 10. The complete system was composed of 10 mM Mn$^{++}$, 0 3% Triton CF-54, 5 mM CDPcholine, 40 μg lactosylceramide, and 1 mM UDP[$^{14}$C]GlcNAc. The dependence on Mn++ was quite strict as substitution with Mg++ and Ca++ yielded 21- and 13-fold less activity, respectively, when present at a final concentration of 10 mM. The metal ion requirement is absolute as substitution of Mn++ with EDTA at 10 mM final concentration abolished all activity. Removal of Triton CF-54 of the exogenous acceptor lactosylceramide greatly diminished the activity. Assays involving relatively crude enzyme preparations routinely contain hydrolytic activities which can either destroy the sugar nucleotide donor or the labeled product. Removal of CDPcholine from the reaction mixture caused a significant loss of activity, whereas inclusion of a β-N-acetylhexosaminidase inhibitor GlcNAc caused only slight stimulation of the activity.

TABLE 10

β1-3N-acetylglucosaminyltransferase reaction requirements

| Condition | pmol/hr/mg protein |
|---|---|
| complete | 76.0 |
| −Mn++, plus Mg++ | 3.6 |
| −Mn++, plus Ca++ | 6.0 |
| −Mn++, plus EDTA | ND |
| −Triton CF-54 | 11.7 |
| −lactosylceramide | 8.3 |
| −CDPcholine | 65.3 |
| +GlcNAc | 80.3 |

The reaction mixtures were as described below under "Experimental Procedures". Divalent metal ions were present at a final concentration of 10 mM. GlcNAc was added at a final concentration of 10 mM.
ND = none detected

Kinetics of β1-3N-acetylglucosaminyltransferase Activity

Figure 12A:
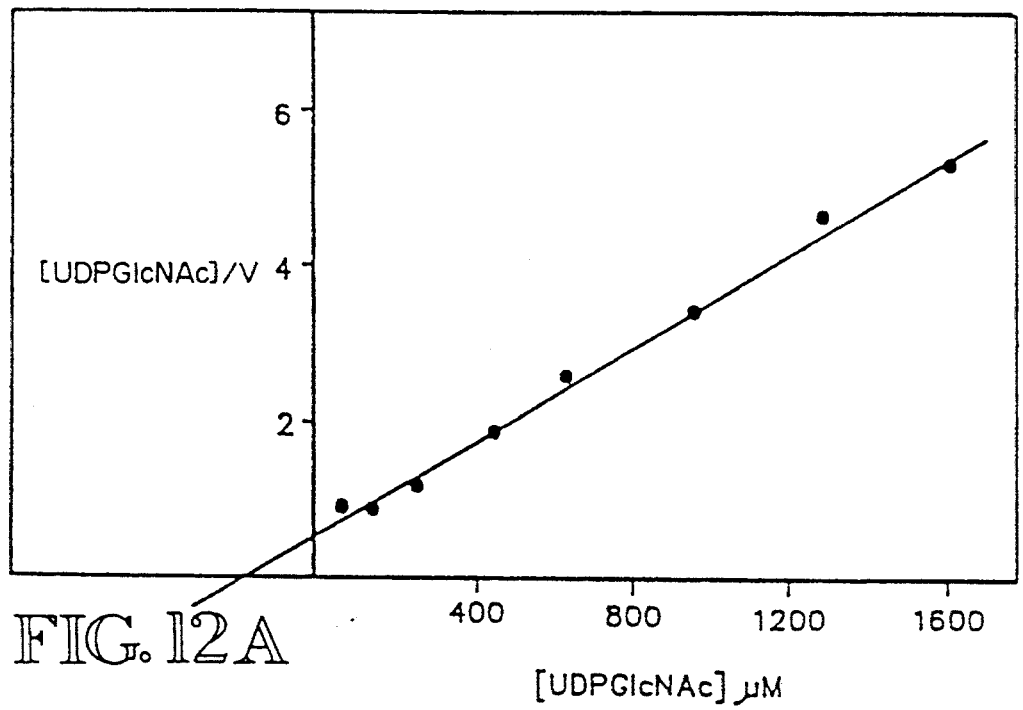
FIG. 12 is a Hanes-Woolf plot of saturation data showing the kinetic parameters from a Hanes-Woolf plot of saturation data with $\beta$1→3N-acetylglucosaminyltransferase. The plot was obtained by varying the concentration of acceptors nLc4, o—o, and nLc6, x—x, from 32 $\mu$M to 640 $\mu$M in the presence of 0.4 mg protein and 50 nmol of UDP[$^{14}$C]GlcNAc per 0.05 ml reaction mixture (FIG. 12A), and by varying the concentration of UDPGlcNAC from 65 μM to 1625 μM in the presence of 0.4 mg protein and 750 μM lactosylceramide (FIG. 12B).

Experiments to define the kinetic constants for various GlcNAc acceptors were conducted. These results are shown in FIG. 12A. A Hanes-Woolf plot of saturation data for acceptors nLc$_4$ and nLc$_6$ indicates essentially equivalent $K_m$ values of 0.19 mM for each. Saturation data for lactosylceramide could not be obtained due to the significant contribution from endogenous acceptor. The $V_{max}$ values determined for nLc$_4$ and nLc$_6$ were 150 and 110 pmol/hr/mg protein, respectively.

Figure 12B:
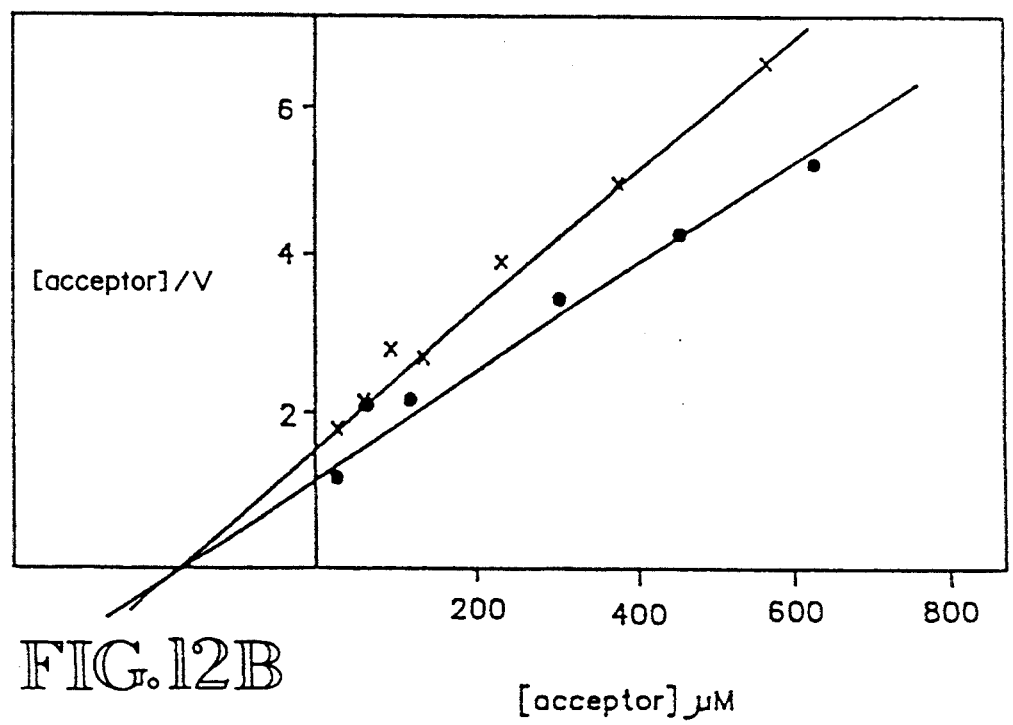

Saturation of the enzyme with UDPGlcNAc with lactosytceramide as the acceptor was also tested as shown in FIG. 12B. The results from a Hanes-Woolf plot of the saturation data indicated a rather high $K_m$ value of 0.17 mM.

Linearity of the Reaction with Time and Protein Concentration

The effect of increasing time and protein on the transfer of GlcNAc to lactosylceramide under the optimal conditions defined above is shown in FIG. 13. Transfer of GlcNAc is proportionate to time of incubation for at least 3 hours (FIG. 13A), and proportionate to the amount of solubilized protein added from 100 to 500 μg per reaction mixture (FIG. 13B).

Acceptor Specificity of SW403 Cell β1-3N-acetylglucosaminyltransferase

The quantitative results from transfer of GlcNAc to several lacto-series glycolipid acceptors is shown in Table 11. The results indicate that transfer to underivatized type 2 lacto-series chains is highest with this enzyme. Transfer to the type 1 chain structure Lc$_4$ is also detectable but is much lower. The enzyme transfers only to underivatized structures as no detectable transfer to any fucosylated derivative of either type 1 or 2 chains was observed.

TABLE 11

Substrate specificity of β1-3N-acetylglucosaminyltransferase

| Acceptor | pmol/hr/mg protein |
|---|---|
| lactosylceramide | 76. |
| nLc$_4$ | 160. |
| Lc$_4$ | 27. |
| nLc$_6$ | 99. |
| III$^3$FucnLc$_4$ | ND |
| V$^3$FucnLc$_6$ | ND |
| III$^3$V$^3$Fuc$_2$nLc$_6$ | ND |
| III$^4$ FucLc$_4$ | ND |

The reaction mixtures were as described under "Experimental Procedures". The assays were conducted in the presence of 40 ug of each acceptor.
ND = none detected

TLC Analysis of Reaction Products from β1-3N-acetylglucosaminyltransferase

FIG. 14 shows the TLC profile of the reaction products from incorporation of [$^{14}$C]GlcNAc into the acceptors described in Table 10. Strong bands are observed from transfer to lactosylceramide, nLc$_4$, and nLc$_6$ and migrate in a position consistent with the addition of a single sugar residue. As described above, formation of a band with Lc$_4$ as the acceptor was found (lane 7) but was much weaker than those with type 2 chain acceptors. Transfer of GlcNAc was determined to be in β1-3 linkage by TLC immunostain analysis using the monoclonal antibody J1 which is specific for terminal β1-3 linked GlcNAc structures (Mol. Immunol., 21, 877–882 (1984)). For these assays, unlabelled GlcNAc was incorporated into lactosylceramide or endogenous acceptor-glycolipids and the products subjected to immunostain analysis. Lanes 10–13 show these results and indicate the transfer of GlcNAc in β1-3 linkage to form Lc$_3$ from lactosylceramide. In addition, hydrolysis of terminally labelled GlcNAc residues from transfer to the acceptors shown in lanes 5–8 was tested. The results indicated that $^{14}$C-labelled GlcNAc was removed by treatment with jack bean β-N-acetylglucosaminidase (results not shown).

DISCUSSION

The results of characterization of this enzyme indicate that it behaves very similarly to the enzyme from serum. Major differences are with respect to the membrane bound nature of the tumor cell enzyme and a higher $K_m$ for UDPGlcNAc compared to the soluble enzyme from serum. Most probably the serum enzyme is a structurally similar enzyme as the membrane bound enzyme and may be released into serum by proteotytic activity.

Fourth Series of Examples

The previous series of examples indicated how one of ordinary skill could evaluate in a diagnostic sense the direct level of activity of β1→3N-acetylglucosaminyltransferase in a tissue or serum specimen. This series of examples describes how one of ordinary skill can also conduct routine techniques leading to other diagnostic tests which form the basis of this application. The general methodology relating to testing levels of expression of β1→3N-acetylglucosaminyltransferase via expression of enzyme protein, mRNA encoding the protein, and by analysis of enzyme reaction products is presented. Each of these test methods would be expected to provide an effective evaluation of the level of β1→3N-acetylglucosaminyltransferase expression.

EXAMPLE 10

Preparation of Antibodies Specific for β1→3N-acetylglucosaminyltransferase

Preparation of antibodies against β1→3N-acetylglucosaminyltransferase protein is based upon use as immunogen of either whole enzyme protein or peptides derived from the whole protein by proteolysis or prepared synthetically based upon a known amino acid sequence.

Two alternate methods providing either mono- or polyclonal antibodies are used, each capable of providing suitable reagents for immunodetection methods. Polyclonal antibodies are prepared by immunizing animals with the purified protein after emulsification with Freund's incomplete adjuvant. Animals are injected subcutaneously one or more times (up to a total of 3 at weekly intervals) with 10–100 μg protein per injection. The serum two weeks after the last injection is collected and the antibody titer determined by either a plate binding method in which purified enzyme protein is adsorbed onto the wells of a 96-well plate, the plate incubated with serial dilutions of antibody, and detection by binding by the antibody of $^{125}$I-protein A, or by the ability of the antibody to neutralize the enzyme activity. The IGg fraction is isolated by DEAE-Sephacel chromatography (*Methods Immunol.*, W. A. Benjamin, Reading, MA, chapter 26 (1977)).

Monoclonal antibodies are produced in mice by immunization with highly purified but not homogeneous enzyme sources. Mice are immunized as above with protein emulsified in Freund's adjuvant three times at weekly intervals with 50–100 μg protein. Spleens are removed and cells fused according to a modification of the method previously described (Selected Methods in Cellular Immunology, pp. 351–372, W. H. Freeman & Co., New York (1980)). X63-Ag8 cells grown in RPMI 1640 medium containing 10% FCS are used as the fusion partner. X63-Ag8 cells, $5 \times 10^7$ are mixed in a ratio of 1:4 with mouse spleen cells prior to fusion with PEG at room temperature. After removal of the PEG and washing the fused cells with fresh medium, the fusion from each spleen are mixed with thymocytes derived from a single thymus in HAT containing RPMI 1640, 10% FCS and plated into 4–96 well culture plates. In order to maintain humidity, the outer wells of each 96 well plate contain serum free medium.

Screening of hybrid cells is conducted initially by solid phase assays with immunogen adsorbed to plastic 96 well plates. Positive clones are detected by autoradiography. Clones showing reactivity with the immunogen are moved to 24 well plates and further tested by neutralization of enzyme activity in order to identify clones binding specifically with the enzyme. The clones showing proper specificity are then further cloned with a thymocyte feeder layer in a ratio of 50 cells per 96 well plate to achieve a uniform antibody producing cell population. Antibody suitable for diagnostic tests are then obtained from culture supernatants.

Immunoassay for β1→3N-acetylglucosaminyltransferase Protein in Serum or Tissue Specimens The presence of β1→3N-acetylglucosaminyltransferase in specimens is assayed using a sandwich immunoassay such as that described below. These procedures are readily applicable to convenient solid phase assays in a diagnostic kit. A sandwich ELISA assay involves depositing the anti-β1→3N-acetylglucosaminyltransferase antibody on a solid support such as a 96-well assay plate. The plate is blocked with 5% BSA in PBS and the test specimen, 50 μl of a serum sample or Triton X-100 solubilized tissue sample, added to the wells and incubated overnight. The PBS washed plates are then incubated with biotinylated-anti-β1→N-acetylglucosaminyltransferase antibody followed by washing and treatment with an avidin-biotin-peroxidase conjugate. After washing, the wells are treated with a mixture of 0.03% $H_2O_2$ containing 1 mM 2,2-azinobis (3-ethylbenzothiazoline-6-sulfonic acid) for 10 minutes and stopped by the addition of 5% SDS. The absorbance at 415 nm is determined. Positive samples are defined as having a significantly higher concentration of antigen when the value is greater than the mean ±2SD of normal samples tested in each assay.

EXAMPLE 11

Isolation of cDNA Probe Specific for β1→3N-acetylglucosaminyltransferase

Initial steps involve isolation of gene sequences encoding the enzyme protein. Two alternate methods may be applied. Using anti-β1→3N-acetylglucosaminyltransferase antibodies, a lambdagt11 cDNA library is screened with the antibody and standard cloning protocols followed (Current Protocols in Molecular Biology, Wiley Interscience, New York, chapter 6 (1987)) to isolate cDNA encoding the protein. Alternatively, mRNA is isolated from a human cell line which expresses this activity and a cDNA library constructed in a mammalian expression vector (Current Protocols in Molecular Biology, Wiley Interscience, New York, chapters 5 & 9 (1987)). Cells which do not express this activity and do not have lacto-series glycolipids such as Kirsten virus transformed mouse 3T3 cells are transfected with the cDNA library. These cells express high levels of asialo-$GM_2$ ($Gg_3$) glycolipid. Incorporation of an active β1→3N-acetylglucosaminyltransferase gene into these cells would initiate synthesis of a lacto-ganglio hybrid structure $LcGg_4$. Cells expressing this structure could be identified and sorted using antibodies YI328-18 or YI328-51, specific for this structure (*J. Biol. Chem.*, 262, 1358–1362 (1987). Plasmid is then isolated from these cells, amplified, and the process repeated until a homogeneous clone encoding this enzyme is isolated. The cDNA sequence is determined according to established procedures (Current Protocols in Molecular Biology, Wiley Interscience, New York, chapter 7 (1987)) and radioactively labeled cDNA probes capable of hybridizing to mRNA encoding the enzyme prepared (Current Protocols in Molecular Biology, Wiley Interscience, New York, chapter 6 (1987)).

Analysis of β1→3N-acetylglucosaminyltransferase Expression in Specimens by Analysis of Specific mRNA Levels Radiolabeled cDNA probes to the β1→3N-acetylglucosaminyltransferase gene are tested by hybridization to mRNA isolated from a tissue specimen of interest using established procedures (Current Protocols in Molecular Biology, Wiley Interscience, New York, chapter 6 (1987>). The level of expression as judged by the amount of labeled probe found to hybridize to the mRNA sample are the basis for comparison. Samples

EXAMPLE 12

Analysis of Expression of β1→3Nacetylglucosaminyltransferase by levels of expression β1→3GlcNAc Containing Reaction Products Because the test activity catalyzes the first committed step in lacto-series glycolipid biosynthesis, elevation of any lacto-series structure would be considered important. Detection of these structures is most conveniently done using antibodies specific for the carbohydrate structures involved. Thus, use of highly specific antibodies against a single structure is unlikely to be useful and should be replaced by antibodies with broad specificity within the lacto-series family or by mixtures of antibodies to broaden the scope of diagnostic analysis. This would be expected to increase the fidelity with which positive samples are discriminated from negative samples using the reaction products as a screening basis.

Examples of suitable antibodies capable of reacting with two or more of such lacto-series carbohydrate epitopes include LcOse$_4$, IV$^3$NeuAcLcOse$_4$, IV$^3$-NeuAcIII$_4$FucLcOse$_4$, III$^4$FucLcOse$_4$, IV$^2$FucLcOse$_4$, III$^4$IV$^2$Fuc$_2$LcOse$_4$, IV$^3$αGalIII$^4$IV$^2$Fuc$_2$-LcOse$_4$, IV$^3$αGalNAcIII$^4$IV$^2$Fuc$_2$LcOse$_4$, nLcOse$_4$, IV$^3$NeuAcnLcOse$_4$, IV$^6$NeuAcnLcOse$_4$, IV$^3$-NeuAcIII$^3$FucnLcOse$_4$, VI$^3$NeuAcIII$^3$V$^3$Fuc$_2$n-LcOse$_6$, III$^3$FucnLcOse$_4$, III$^3$V$^3$Fuc$_2$nLcOse$_6$, IV$^2$-FucnLcOse$_4$, III$^3$IV$^2$Fuc$_2$nLcOse$_4$, III$^3$V$^3$VI$^2$Fuc$_3$n-LcOse$_6$, IV$^3$αGalIII$^3$IV$^2$Fuc$_2$nLcOse$_4$, and IV$^3$αGal-NAcIII$^3$IV$^2$Fuc$_2$nLcOse$_4$.

Monoclonal antibodies versus glycolipids are prepared in mice after immunization as previously established (*J. Biol. Chem.*, 259, 4681–4685 (1985)) and cloned as described for the enzyme protein-except that purified glycolipid is used for antibody screening. Antibodies with both narrow and broad specificity within the lacto-series family can be obtained in this manner.

Use of broadly specific antibodies or mixtures are applied to immunoassay of specimens such as serum samples as described above for the β1→3N-acetylglucosaminyltransferase enzyme protein. Alternatively, a direct assay of β1→3-linked GlcNAc structures using terminal GlcNAc-specific antibodies could be applied to immunoassay of specimens after first treating the specimen with specific glycohydrolase enzymes either sequentially or mixed together. Since the variety of lacto-series structures present in tumors generally contain sialylated and/or fucosylated modifications of type 1 or 2 lacto-series chains, treatment with Vibrio cholerae neuraminidase, bovine kidney fucosidase, and jack bean β-galactosidase generates terminal GlcNAc containing structures for antibody detection. Conditions for this treatment would involve incubation of the specimen with the above enzymes in 100mM citrate buffer, pH 5.5 for 1 to 2 hours prior to antibody assay.

Discussion

This series of examples describes a practical basis for the use of the level of expression of β1→3N-acetylglucosaminyltransferase for diagnosis of the disease status of an individual using a tissue or serum specimen. Given that the induction of lacto-series tumor associated antigen synthesis in human secretory epithelia is due to activation of β1→3N-acetylglucosaminyltransferase, multiple alternate methods for determining its expression level exist. One strategy may be more practical than another but the outcome would in each case depend on the level of enzyme expression.

EXPERIMENTAL PROCEDURES

Materials

Normal human colonic mucosa was obtained from two individuals of blood group B and one of blood group. 0. Human small cell lung carcinoma NCI-H69 cell line was obtained from the American Type Culture Collection (Rockville, Md.). GDP[$^{14}$C]fucose (28 mCi/mmol) and UDP[$^{14}$C]-galactose (240 mCi/mmol) were obtained from Amersham (Arlington Heights, Ill.). Unlabelled GDPfucose was prepared by the method of Ginsburg (*Methods Enzymol.*, 293-295 (1966)). Unlabelled UDPgalactose was obtained from Sigma (St. Louis, Mo.). Type 2 chain glycolipids nLc$_4$ and nLc$_6$ were prepared by desialylation of sialosyllactoneotetraosylceramide and sialosyllactonorhexaosylceramide, which were prepared from bovine erythrocytes (*J. Biol. Chem.*, 253, 4031–4035 (1978)). Desialylation was performed in 1% acetic acid at 100° C. for 1 hour. Lc$_3$ was prepared from nLc$_4$ by overnight hydrolysis with jack bean β-galactosidase in 0.1M citrate buffer, pH 4.5, containing 0.1% deoxycholate. Glycolipids with the Le$^x$ hapten structure, III$^3$FucnLc$_4$, V$^3$FucnLc$_6$, and III$^3$V$^3$Fuc$_2$nLc$_6$, were prepared from human colonic adenocarcinoma (*J. Biol. Chem.*, 259, 4672–4680 (1984)). Lactotetraosylceramide (type 1 chain paragloboside) (*J. Biol. Chem.*, 254, 9311–9316 (1979)) was isolated from human meconium. The monoclonal antibodies FH3, 1B2, BE2, and AH6 were obtained as previously described (*J. Biol. Chem.*, 259, 4681–4685 (1984), *J. Biol. Chem.*, 256, 10967–10972 (1981), *J. Biol. Chem.*, 258, 11793–11979 (1983)), and WGHS-29-1 (*Arch. Biochem. Biophys.*, 217, 647–651 (1982)), which reacts with Le$^x$ determinants, was a gift from Dr. Hilary Koprowski, The Wistar Institute, Philadelphia, Pa. Anti-Le$^a$ antibodies were obtained from Chembiomed Ltd., Edmonton, Alberta. The cationic detergent G-3634-A was a gift from Dr. Subhash Basu, Notre Dame University, South Bend, Ind. All other reagents were of the highest purity commercially available.

METHODS

Cell Culture

Cell lines PC9, NCI-H69, DLD-1, HCT-15, and Colo 205 were grown in RPMI 1640 medium supplemented with 10% fetal calf serum. The cell lines SW403, SW480, SW948, and SW1417 were grown in L-15 medium supplemented with 10% fetal calf serum. HCMC cells were grown in MEM medium containing nonessential amino acids in Earle's BSS, 20% fetal calf serum, and 10 ng/ml epidermal growth factor. These cells have been reported to be epithelial in origin, presumably from the lower two-thirds of the crypt (*J. Natl. Cancer Inst.*, 69, 1271–1276 (1982)). The cells were harvested and passed every 7-10 days. The cells were scraped, centrifuged, and washed with phosphate-buffered saline (PBS), and stored frozen at −80° C.

Solubilization of Glycosyltransferase Activities from NCI-H69 Cells

The following steps were performed at 0°–4° C. Cells, 6 ml, were thawed and homogenized in two volumes of 50 mM HEPES buffer, pH 7.2, 0.5 M sucrose, 1 mM EDTA by two strokes of a Potter-Elvehjem homogenizer. The crude homogenate was centrifuged at 27,000 xg for 30 minutes to separate membranes from soluble proteins. The resulting pellet fraction was then re-homogenized in the presence of two volumes of the above buffer containing Triton X-100 at 0.2% final concentration with two strokes of the homogenizer and centrifuged for 1 hour at 100,000 xg. T-he supernatant fraction was removed and the 0.2% Triton X-100 extraction step was repeated with an additional two volumes of the Triton X-100 containing buffer. The pooled supernatant fractions were then concentrated to the original volume of packed cells by ultrafiltration and centrifugation through a conical nitrocellulose membrane (Amicon Centraflo CF 25 membranes, Amicon Corp., Lexington, Mass. 02173). Except where indicated, the concentrated enzyme fraction was used for characterization of activities present in NCI-H69 cells. The enzyme could be stored frozen at $-20°$ C. without considerable loss of activity.

Preparation of Normal Human Colonic Mucosa Fraction

Samples of normal colon were obtained and stored frozen at $-80°$ C. before use. The thawed tissue was washed extensively in PBS and the mucosal lining was scraped off by the sharp edge of a piece of objective glass, washed three times with PBS, and centrifuged at 2000 xg for 5 minutes at 4° C. A portion of each mucosal fraction was homogenized in two volumes of 50 mM HEPES buffer, pH 7.2, 0.5M sucrose, 1 mM EDTA by two strokes of a Potter-Elvehjem homogenizer and used for characterization of enzyme activities present in normal colonic mucosa. Another portion of the mucosal fractions from the type "B" individuals was pooled and the glycolipids extracted as described below.

Extraction of Glycolipids from Tissues and Cells

Glycolipids were isolated from 5 ml each of packed NCI-H69 cells and normal human colonic mucosal residue by extraction with 10 volumes of isopropanol/hexane/water (55:25:20) in a Waring blender followed by filtration in a Buchner funnel. The insoluble residue was re-extracted with 10 volumes of the same solvent followed by filtration. The combined filtrates were concentrated to near dryness and transferred to Spectrapor 3 membrane tubing (Spectrum Medical Industries, Los Angeles, Calif.) and dialyzed extensively against water. The solution was removed from the dialysis bag and concentrated to near dryness and dissolved in a solvent composed of $CHCl_3:CH_3OH:H_2O$ (30:60:8) and subjected to chromatography on DEAE-Sephadex A-25 according to the method of Yu and Ledeen (*J. Lipid Res.*, 13, 680–686 (1972)) to separate neutral glycolipids from gangliosides. The neutral glycolipid fraction obtained from the passthrough of the DEAE-Sephadex column was concentrated to dryness and placed in a vacuum dessicator over $P_2O_5$ overnight followed by acetylation with 10 ml of pyridine and 5 ml of acetic anhydride. The acetylated glycolipid fraction was obtained by chromatography on a Fluorisil column (*J. Lipid Res.*, 12, 257–259 (1971)). The deacetylated neutral glycolipid fractions and the dialyzed total ganglioside fractions obtained from DEAE-Sephadex chromatography were utilized in these studies.

Glycolipids from type O erythrocytes and tumor tissue were obtained as previously described (*J. Biol. Chem.*, 259, 4672–4680 (1984)).

Enzyme Assays

α1-3Fucosyltransferase

Unless otherwise specified, the α1-3fucosyltransferase activity was determined in reaction mixtures containing 2.5 μmol HEPES buffer, pH 7.2, 40 μg $nLc_4$, 100 μg G-3634-A, 1 μmol $MnCl_2$, 0.5 μmol CDPcholine, 15 nmol $GDP[^{14}C]$-fucose (15,000 cpm/nmol), and 15–150 μg protein in a total volume of 0.1 ml. The reaction mixture was incubated for 2 hours at 37° C. for 2 hours and terminated by the addition of 6 μmol of EDTA and 0.1 ml of $CHCl_3:CH_3OH$, 2:1. The entire reaction mixture was streaked onto a 4 cm wide strip of Whatman 3 paper and chromatographed with water overnight. The glycolipid remaining at the origin was extracted with 2–5 ml washes of $CHCl_3:CH_3OH:H_2O$, (10:5:1). The solvent was removed with a nitrogen stream and dissolved in 20 μl $CHCl_3:CH_3OH$ (2:1). An aliquot, 10 μl, was removed and spotted onto an HPTLC plate (Merck, Darmstadt, West Germany) and developed in a solvent of $CHCl_3:CH_3OH:H_2O$ (60:40:9) containing 0.02% $CaCl_2$ as a final concentration. Standard glycolipids were visualized by orcinol spray. Radioactive glycolipid bands were located by autoradiography, scraped from the plate, and counted by a liquid scintillation counter. One unit of activity is defined as transfer of one pico mol of fucose per hour under the conditions of the assay.

β1-3 and β1-4Galactosyltransferase

The reaction mixtures contained 2.5 μmol HEPES buffer, pH 7.0, 20 μg $Lc_3$, 10 μg deoxycholate, 1 μmol $MnCl_2$, 0.5 μmol CDPcholine, 0.5 μmol galactonolactone, 15 nmol $UDP[^{14}C]$galactose (30,000 cpm/nmol), and 0.1 mg protein in a total volume of 0.1 ml. The reaction was conducted for 1 hour at 37° C. and stopped by the addition of 6 μmol of EDTA and 100 μl of $CHCl_3:CH_3OH$ (2:1). The incorporation of $[^{14}C]$galactose into glycolipid was determined as described above.

β1→3N-acetylglucosaminyltransferase

N-acetylglucosaminyltransferase assays were performed in reaction mixtures containing 2.5 μmol of HEPES buffer, pH7 2, 30 μg of lactosylceramide, 150 μg of Triton CF-54, 0.5 μmol of $MnCl_2$, 0.5 μmol of CDPcholine, 50 nmol of $UDP[^{14}C]$N-acetylglucosamine (5000 cpm/nmol), and 200–400 μg of protein in a total volume of 0.05 ml. The reaction mixture was incubated for 2 hours at 37° C. and terminated by addition of 50 μl of 0.25M EDTA and 0.6 ml $CHCl_3:CH_3OH$ (2:1). The labelled product was extracted into the lower phase of a Folch extraction (*J. Biol. Chem.*, 191, 819–831), dried by an $N_2$ stream, and dissolved in 20 μl of $CHCl_3:CH_3OH$ (2:1). An aliquot, 10 μl was spotted on a HPTLC plate (Merck) and developed in a solvent composed of $CHCl_3:CH_3OH:H_2O$ (60:35:8). The labelled glycolipids were located by autoradiography, scraped, and quantitated in a liquid scintillation counter.

Protein Determination

Protein concentrations were determined by the method of Lowry et al. (*J. Biol. Chem.*, 193, 265–275 (1951)) using a bovine serum albumin standard.

Immunostaining of Glycolipids

Immunostaining of glycolipids separated on HPTLC plates was performed using the procedure of Magnani et al. (*Anal. Biochem.*, 109, 399–402 (1980)) as modified by Kannagi et al. (*J. Biol. Chem.*, 257, 14865–14874 (1982)). Glycolipids were separated on an HPTLC plate (Si-HPTLC plate 7011-3, J. T. Baker Chemical Co., Phillipsburg, N.J.) using solvent systems composed of $CHCl_3:CH_3OH:H_2O$ (60:35:8), $CHCl_3:CH_3OH:H_2O$ (56:38:10), and $CHCl_3:CH_3OH:H_2O$ (60:40:9) containing 0.02% $CaCl_2.2H_2O$. After development, the plate was dried and soaked for 2 hours in 5% bovine serum albumin in PBS to block nonspecific antibody binding. The plate was then incubated in a 1:500 to 1:1000 diluted monoclonal antibody in PBS containing 1% bovine serum albumin overnight, followed by sequential incubations with 1:2000 diluted rabbit anti-murine Ig antibody solution and with [$^{125}$I]-protein A solution. After extensive washes with PBS between each step and after [$^{125}$I]-protein A treatment, the plate was dried and labelled bands were detected by autoradiography. Immunostain analysis of products from enzyme reactions were performed in the same way. The in vitro synthesized products were prepared using the assay conditions already described except that unlabeled sugar nucleotide donors were utilized. In each case control reaction mixtures without addition of exogenous glycolipid acceptor were run to monitor amounts of endogenous glycolipid staining.

Immunofluorescence Studies of Normal Human Fetal and Adult Colon Tissue

Fresh samples of normal adult proximal colon and fetal intestinal tissue were obtained and prepared for cryostat sectioning. The sections were incubated with primary antibody specific for either Le$^x$, Le$^a$, or type 2 chain lacto-structures both before and after treatment of the tissue with C. perfringes neuraminidase. The sections were washed and treated with FITC-labelled secondary antibody. The washed sections were then examined by fluorescence microscopy.

in situ Biosynthesis of nLc$_4$ in Normal Colon Tissue Sections

Surgical samples of normal colon from patients with non-malignant disease were obtained and immediately frozen for cryostat sectioning. Sections, 6 microns thick, were cut and washed in PBS. Glycolipids (Lc$_3$, nLc$_4$, or Gg$_4$) were adsorbed to the membranes of some of the sections by incubation in the presence of 0.1 mg glycolipid per ml of PBS for 4 hours at 4° C. At the end of this period, the sections were washed in PBS three times and finally in 50 mM HEPES buffer, pH7.0. An aliquot, 100 μl, of a reaction mixture containing 2.5 μmol HEPES buffer, pH 7.0, 1 μmol $MnCl_2$, 0.5 μmol CDPcholine, 0.5 μmol galactonolactone, with or without 50 nmol UDPgalactose was layered over the appropriate tissue section and incubated for 3 hours at room temperature. The sections were then washed three times in PBS followed by incubation for 1 hour in PBS containing 5% goat serum. At the end of this period, 100 μl of antibody 1B2 ascites diluted 1:100 in PBS containing 0.5% goat serum was layered over the tissue and incubated overnight at room temperature. After washing with PBS, the tissue was incubated with 1:40 diluted FITC-labelled rabbit anti-mouse whole Ig for 1 hour, washed extensively with PBS, and mounted for examination by fluorescence microscopy. Control tissue sections were run which contained either no or an irrelevant glycolipid (Gg$_4$) and also with and without UDPgalactose in the reaction mixture.

I claim:

1. A method for identifying a premalignant or malignant state in secretory epithelia of a human subject comprising the steps of:
   a) obtaining a test specimen from the human subject;
   b) evaluating the levels of an active or expressed β1-3N-acetylglucosaminyltransferase enzyme in the test specimen by evaluating the level of GlcNAcβ1-3Gal linkages in glycoproteins or glycolipids, an elevated level of the active or expressed enzyme indicating a premalignant or malignant state in the human subject.

2. The method of claim 1 wherein the premalignant or malignant state of secretory epithelia is related to colonic adenocarcinoma.

3. The method of claim 1 wherein the premalignant or malignant state of secretory epithelia is related to cancers that produce lacto-series 1 antigens.

4. The method of claim 1 wherein the premalignant or malignant state of secretory epithelia is related to cancers that produce lacto-series 2 antigens.

5. The method of claim 1 wherein the premalignant or malignant state of secretory epithelia is related to cancers that produce lacto-series 1 and lacto-series 2 antigens.

6. A method for diagnostic or prognostic detection of a cancerous disease state in human secretory epithelia comprising evaluating the levels of β1-3N-acetylglucosaminyltransferase expression in a test specimen by evaluating the level of GlcNAcβ1-3Gal linkages in glycoproteins or glycolipids wherein an increase in β1-3N-acetylglucosaminyltransferase expression is observed in a cancerous disease state as compared with a healthy state.

7. The method of claim 6 wherein the cancerous disease state of secretory epithelia is related to colonic adenocarcinoma.

8. The method of claim 6 wherein the cancerous disease state of secretory epithelia is related to cancers that produce lacto-series 1 antigens.

9. The method of claim 6 wherein the cancerous disease state of secretory epithelia is related to cancers that produce lacto-series 2 antigens.

10. The method of claim 6 wherein the cancerous disease state of secretory epithelia is related to cancers that produce lacto-series 1 and lacto-series 2 antigens.

11. A method for identifying a premalignant or malignant state in secretory epithelia of a human subject comprising the steps of:
   a) obtaining a test specimen from the human subject;
   b) assaying for an active or expressed β1-3N-acetylglucosaminyltransferase enzyme in the test specimen by evaluating the level of GlcNAcβ1-3Gal linkages in glycoproteins or glycolipids; and
   c) comparing the levels to that of a healthy test specimen, the presence of an elevated level of the active or expressed enzyme as compared to that of a healthy test specimen indicating a premalignant or malignant state in the human subject.

12. The method of claim 11 wherein the premalignant or malignant state of secretory epithelia is related to colonic adenocarcinoma.

13. The method of claim 11 wherein the premalignant or malignant state of secretory epithelia is related to cancers that produce lacto-series 1 antigens.

14. The method of claim 11 wherein the premalignant or malignant state of secretory epithelia is related to cancers that produce lacto-series 2 antigens.

15. The method of claim 11 wherein the premalignant or malignant state of secretory epithelia is related to cancers that produce lacto-series 1 and lacto-series 2 antigens.

* * * * *